United States Patent
Vu et al.

(10) Patent No.: US 10,473,667 B2
(45) Date of Patent: Nov. 12, 2019

(54) METHODS APPARATUSES AND SYSTEMS FOR DETECTING AND QUANTIFYING PHOSPHOPROTEINS

(71) Applicants: Tania Vu, Portland, OR (US); Thomas Jacob, Beaverton, OR (US); Brian J Druker, Portland, OR (US)

(72) Inventors: Tania Vu, Portland, OR (US); Thomas Jacob, Beaverton, OR (US); Brian J Druker, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 349 days.

(21) Appl. No.: 15/175,434

(22) Filed: Jun. 7, 2016

(65) Prior Publication Data

US 2016/0377627 A1 Dec. 29, 2016

Related U.S. Application Data

(63) Continuation of application No. 14/019,829, filed on Sep. 6, 2013, now abandoned, and a continuation of application No. PCT/US2012/028123, filed on Mar. 7, 2012.

(51) Int. Cl.
| | | |
|---|---|---|
| G01N 33/48 | (2006.01) | |
| G01N 31/00 | (2006.01) | |
| G01N 33/58 | (2006.01) | |
| G01N 33/68 | (2006.01) | |
| G01N 33/574 | (2006.01) | |
| B82Y 15/00 | (2011.01) | |

(52) U.S. Cl.
CPC ..... *G01N 33/588* (2013.01); *G01N 33/57426* (2013.01); *G01N 33/57484* (2013.01); *G01N 33/57496* (2013.01); *G01N 33/587* (2013.01); *G01N 33/6842* (2013.01); *B82Y 15/00* (2013.01); *G01N 2333/47* (2013.01); *G01N 2440/14* (2013.01); *G01N 2500/20* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 3,578,604 A | 5/1971 | Uriel | |
| 7,052,915 B2 | 5/2006 | Aebersold et al. | |
| 7,309,569 B2 | 12/2007 | Oshida et al. | |
| 7,799,526 B2 | 9/2010 | Howe | |
| 2002/0028457 A1 | 3/2002 | Empedocies et al. | |
| 2005/0148100 A1 | 7/2005 | Su et al. | |
| 2007/0111225 A1 | 5/2007 | Lambert et al. | |
| 2007/0159624 A1 | 7/2007 | Resch-Genger et al. | |
| 2008/0220982 A1 | 9/2008 | Vu | |
| 2009/0277791 A1 | 11/2009 | Vu et al. | |

FOREIGN PATENT DOCUMENTS

| | | |
|---|---|---|
| WO | 2006070180 A1 | 7/2006 |
| WO | 2007015886 A2 | 2/2007 |
| WO | 2008051985 A2 | 5/2008 |
| WO | 2010127114 A2 | 11/2010 |

OTHER PUBLICATIONS

International Search Report, PCT/US2012/028123, dated Sep. 19, 2013.
Kinoshita et al., Separation and detection of large phosphoproteins using Phos-tag SDS-PAGE, Nature Protocols, vol. 4, No. 10, 2009, pp. 1513-1521.
Bodo et al., Quantitative In Situ Detection of Phosphoproteins in Fixed Tissues Using Quantum Dot Technology, J Histochemistry & Cytochemistry, vol. 57(7), 2009, pp. 701-708.
Casanova et al, "Counting the number of proteins coupled to single nanoparticles," Journal of the American Chemical Society 129, 12592-12593 (2007).
Lagerholm et al.,Analysis Method for Measuring Submicroscopic Distances with Blinking Quantum Dots Biophysical Journal 91 3050-3060 (2006).
Scholl B et al, "Single Particle Quantum Dot Imaging Achieves Ultrasensitive Detection Capabilities for Western Immunoblot Analysis," ACS Nano 3, 1318-1328 (2009).
Tibbe Agj et al, "Optical tracking and detection of immunomagnetically selected and aligned cells," Nature Biotechnology 17, 1210-1213 (1999).
Pinwattana et al., CdSe/ZnS quantum dots based electrochemical immunoassay for the detection of phosphorylated bovine serum albumin, Biosensors and Bioelectronics, 26, 2010, pp. 1109-1113.

*Primary Examiner* — Anna Skibinsky

(57) ABSTRACT

Embodiments herein provide methods, apparatuses, and systems for detecting, monitoring, measuring, and/or characterizing the activity of phosphoproteins such as tyrosine kinases (TKs) and downstream proteins in TK signal transduction pathways (e.g., TK pathway proteins). In various embodiments, the methods, apparatuses, and systems may use nanoparticles, such as quantum dots (QD), to detect and/or characterize the abnormally overactive TK signaling pathways that underlie tumorgenesis and tumor progression. In various embodiments, the QD-based methods, apparatuses, and systems may have a sufficiently high degree of sensitivity to enable the identification of new TK signaling pathway markers, for example for use in diagnosing, staging, monitoring, and/or prognosing cancers, or in evaluating the efficacy of cancer therapeutics.

11 Claims, 19 Drawing Sheets

Schematic of 3-D imaging system

Schematic of Z-stack imaging

Figure 4A
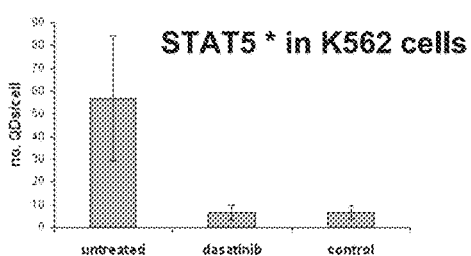
Figure 4B
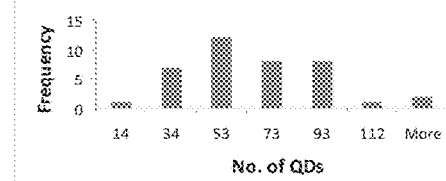
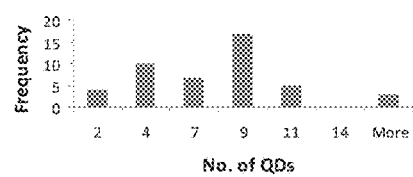
Figure 4C
Figure 4D

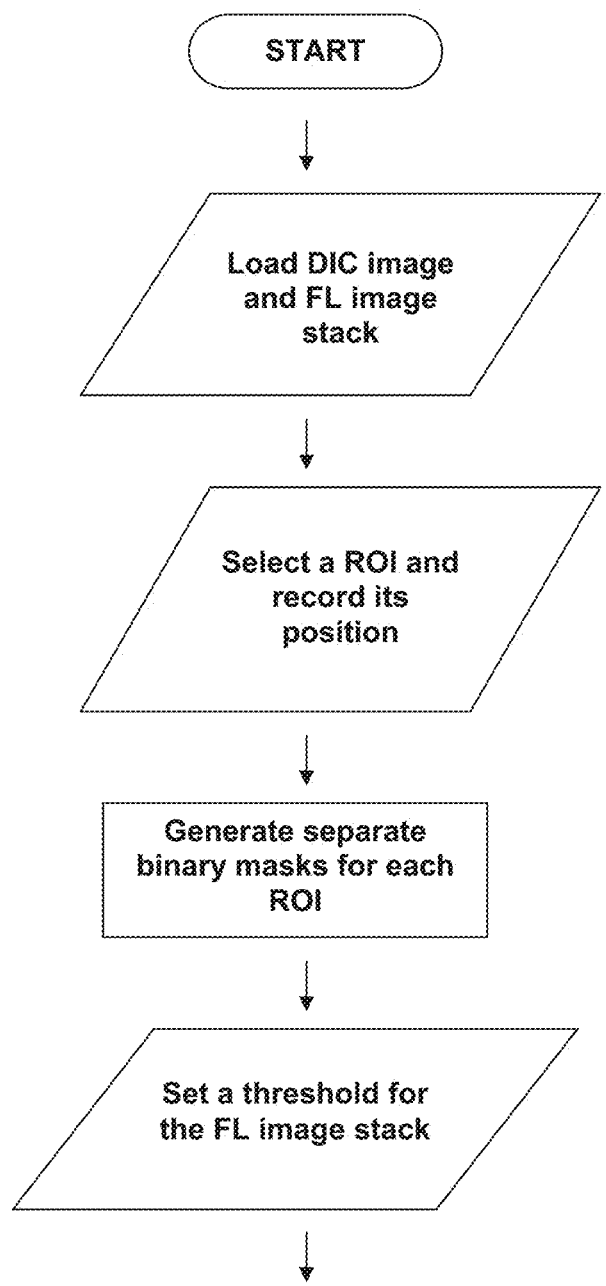

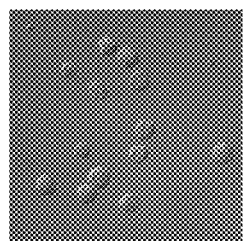
DIC image
Figure 8A
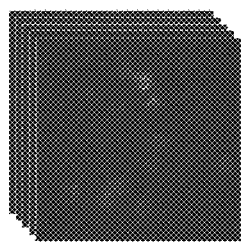
FL image stack
Figure 8B
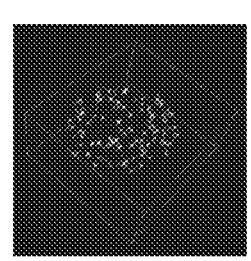
QD distribution
in a cell
Figure 8C
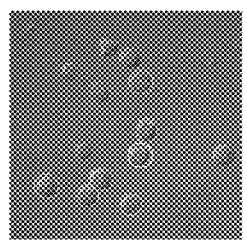
User marked
DIC image
Figure 8D
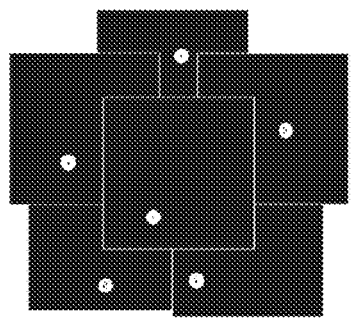
Binary masks
representing each
marked ROI
Figure 8E
Example of a
binary mask
Figure 8F

METHODS APPARATUSES AND SYSTEMS FOR DETECTING AND QUANTIFYING PHOSPHOPROTEINS

CROSS REFERENCE TO RELATED APPLICATIONS

The present application is a continuation of U.S. patent application Ser. No. 14/019,829 filed September 6, 2013, now abandoned. The present application claims priority to U.S. Provisional Patent Application No. 61/449,896, file Mar. 7, 2011, entitled "METHODS, APPARATUSES, AND SYSTEMS FOR DETECTING AND QUANTIFYING PHOSPHOPROTEINS," the disclosure of which is hereby incorporated by reference in its entirety.

The present application is also related to PCT Patent Application No. WO/2010127114, filed Apr. 29, 2010, entitled "AUTOMATED DETECTION AND COUNTING OF BIOMOLECULES USING NANOPARTICLE PROBES," and U.S. Provisional Patent Application No. 61/174,924, filed May 1, 2009, the disclosures of which are hereby incorporated by reference in their entirety.

TECHNICAL FIELD

Embodiments herein relate to the field of biomolecule detection, and more specifically, to methods, apparatuses, and systems for detecting phosphoprotein activation using nanoparticle probes, such as quantum dots.

BACKGROUND

Cancer treatment has undergone dramatic changes in the past decade. The efficacy of imatinib (Gleevec™) in suppressing tumor growth has initiated a paradigm shift in drug development toward the use of cancer therapeutics with well-defined molecular targets. An increasing number of drugs are being developed to inhibit various mutant tyrosine kinases (TK). Notably, TKs are critical regulators of downstream signaling pathways that control tumor growth.

To date, the greatest clinical success of TK inhibitors has been in the treatment of malignancies with genomic mechanisms of TK target activation (e.g., CML and BCR-ABL, GIST and KIT). However, further research into common tumors has demonstrated a marked heterogeneity in underlying genomic mutations that activate signaling pathway proteins. This heterogeneity complicates the rapid identification of patients likely to benefit from treatment with a given targeted agent since increasing numbers of genomic loci must be analyzed for mutations. Moreover, the current generation of TK inhibitors (TKIs) may provide initial suppression of tumor growth, but may not be able to prevent relapse since secondary resistance is known to develop. This is in part due to the selective expansion of initial drug-resistant mutant TKs, which provokes new tumor growth. Further, while a TKI may successfully suppress upstream signaling pathways, resistance may develop from signaling via alternate downstream segments of signaling cascades.

BRIEF DESCRIPTION OF THE SEVERAL VIEWS OF THE DRAWINGS

Embodiments will be readily understood by the following detailed description in conjunction with the accompanying drawings. Embodiments are illustrated by way of example and not by way of limitation in the figures of the accompanying drawings.

FIGS. 4A-4D illustrate a graph showing the number of QD particles per cell in dasatinib-treated and untreated K562 cancer cells (FIG. 4A), a digital image of QD-STAT5* labeling in dasatinib-treated and untreated K562 cancer cells (FIG. 4B), histograms showing the number of QD particles per cell in untreated (FIG. 4C) and dasatinib-treated (FIG. 4D) K562 cancer cells, in accordance with various embodiments;

FIGS. 8A-8J illustrate the method shown in FIGS. 2A-2E in greater detail, in accordance with various embodiments;

DETAILED DESCRIPTION OF SEVERAL EMBODIMENTS

Figure 1A:
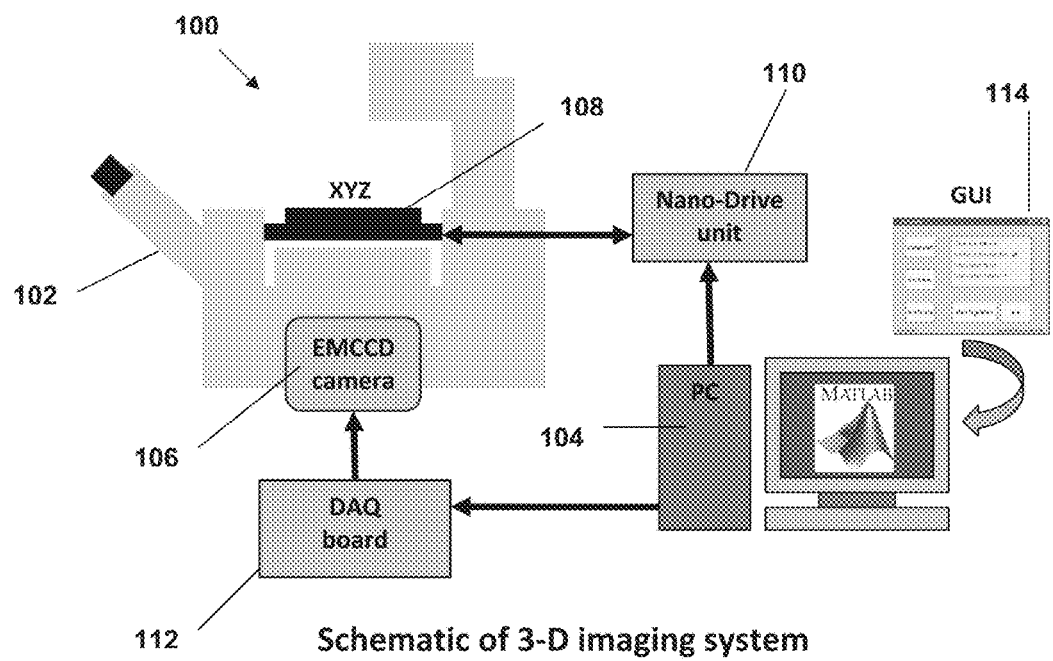
FIGS. 1A-1B illustrate a schematic of a 3-D imaging system (FIG. 1A) and a schematic of Z-stack imaging (FIG. 1B), in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, methods, apparatuses, and systems for identifying, monitoring, and characterizing phosphoprotein activity are provided. In exemplary embodiments, a computing system may be endowed with one or more components of the disclosed apparatuses and/or systems and may be employed to perform one or more methods as disclosed herein.

Embodiments herein provide methods, apparatuses, and systems for detecting, monitoring, measuring, and/or characterizing the activity of phosphoproteins, such as tyrosine kinases (TKs) and downstream proteins in TK signal transduction pathways (e.g., TK pathway proteins). In various embodiments, the methods, apparatuses, and systems may use nanoparticles, such as quantum dots (QD), to detect and/or characterize abnormally overactive TK signaling pathways that underlie tumorgenesis and tumor progression. In various embodiments, the QD-based methods, apparatuses, and systems may have a sufficiently high degree of sensitivity to enable the identification of new TK signaling pathway markers, for example for use in diagnosing, staging, monitoring, and/or prognosing cancers, or in evaluating the efficacy of cancer therapeutics.

Additionally, in some embodiments, the nanoparticle-based methods, apparatuses, and systems may facilitate the development of new TKI-based therapies that may overcome the drug resistance, disease relapse, and/or eventual formation of new tumors that may occur with existing TKI-based therapeutics. In various embodiments, these methods, apparatuses, and systems may allow detection and quantification of phosphoproteins at a molecular level of resolution in single cells and tissues. Also disclosed in some embodiments are methods and systems for using computational high-throughput algorithms to quantify phosphoproteins and/or phosphoprotein activity. Such systems and methods may be used for cancer staging, monitoring the effectiveness of therapies, and/or for biomarker identification, in various embodiments.

Thus, provided in various embodiments are methods for detecting phosphoprotein activity in a sample, such as a tissue sample, cell sample, or bodily fluid sample. In some embodiments, the phosphoprotein being detected and/or quantified may be a TK pathway protein, for instance an activated protein in a TK signaling sequence that is thought to be involved in tumorgenesis or tumor progression. In various embodiments, the method may include contacting the sample with one or more specific binding agents, such as an antibody specific for the activated protein of interest, wherein the specific binding agent may be conjugated to a nanoparticle, such as a QD. In various embodiments, the method also may include processing the sample to reduce non-specific binding of the specific binding agent, and detecting or quantifying the nanoparticle, thereby detecting/quantifying the activated TK pathway protein. In some embodiments, the method also may include comparing the amount of the activated TK pathway protein detected with a reference number or sample.

Embodiments also may provide automated methods and systems for processing the sample, and automated methods and systems for detecting or quantifying a TK pathway protein in the sample. In various embodiments, these methods may include labeling an activated TK pathway protein with a nanoparticle probe that includes a detectable nanoparticle, providing the labeled activated TK pathway protein on a transparent base material, and automatically counting the nanoparticles. In some embodiments, automatically counting the nanoparticles may include automatically capturing an image of the nanoparticles in each of several XYZ positions in the sample, automatically detecting nanoparticles that have fluoresced in the images, and maintaining a count of discrete groups of nanoparticle probes or single nanoparticle probes, wherein counting the nanoparticles is considered counting the target biomolecules. In some embodiments, the method may also include adjusting the nanoparticle count to avoid double-counting of nanoparticles that appear in more than one image.

To facilitate review of the various embodiments of the disclosure, the following explanations of specific terms are provided:

As used herein, the term "aptamer" refers to a small nucleic acid or peptide molecule that may bind a specific target molecule, such as a target biomolecule.

As used herein, the term "automated," "automatic," and "automatically" refer to a process that may be carried out without input for with minimal input) from a user, such as a process that is carried out under the control or operation of a computing system.

As used herein, the term "detect" means to determine whether an agent (such as a signal or particular molecule) is present or absent. In some examples, this may further include quantification. The use of nanoparticle probes in particular examples may permit detection of a target biomolecule, for example detection of a signal from a nanoparticle probe may be used to detect the presence of a target biomolecule of interest that is labeled with the nanoparticle probe. In some examples, a single nanoparticle probe may be detected, for example, in some embodiments, a single semiconductor nanocrystal may be detected.

As used herein, the term "electromagnetic radiation" refers to a series of electromagnetic waves that may be propagated by simultaneous periodic variations of electric and magnetic field intensity, including radio waves, infrared, visible light, ultraviolet light, X-rays, and gamma rays. In particular examples, electromagnetic radiation may be emitted by a laser, which may possess properties of monochromaticity, directionality, coherence, polarization, and intensity. Lasers are capable of emitting light at a particular wavelength (or across a relatively narrow range of wavelengths).

As used herein, the term "emission" or "emission signal" refers to the light of a particular wavelength generated from a source. In particular examples, an emission signal may be emitted from a semiconductor nanocrystal after the fluorophore absorbs light at its excitation wavelengths.

As used herein, the term "excitation" or "excitation signal" refers to the light of a particular wavelength necessary and/or sufficient to excite an electron transition to a higher energy level. In particular examples, an excitation may be the light of a particular wavelength necessary and/or sufficient to excite a fluorophore to a state such that the fluorophore, such as a semiconductor nanocrystal, may emit a different (such as a longer) wavelength of light then the wavelength of light from the excitation signal.

As used herein, the term "label" refers to an agent capable of detection, for example by spectrophotometry, flow cytometry, or microscopy. For example, in some embodiments, a label may be attached to a specific binding agent, such as an antibody or a protein, thereby permitting detection of a biomolecule bound to the specific binding agent. Specific, non-limiting examples of labels include fluorescent tags, enzymatic linkages, and radioactive isotopes and nanoparticles, such as semiconductor nanocrystals. In some embodiments, the label may be a nanoparticle, such as a semiconductor nanocrystal. Methods for labeling are discussed, for example, in Sambrook et al. (*Molecular Cloning: A Laboratory Manual*, Cold Spring Harbor, N.Y., 1989) and Ausubel et al. (*Current Protocols in Molecular Biology*, John Wiley & Sons, New York, 1998).

As used herein, the term "linker" refers to a compound or moiety that may act as a molecular bridge to operably link two different molecules, wherein one portion of the linker is operably linked to a first molecule, and wherein another portion of the linker is operably linked to a second molecule. In various embodiments, the two different molecules may be linked to the linker in a stepwise manner. There are no particular size or content limitations for the linker, so long as it may fulfill its purpose as a molecular bridge. Linkers are known to those skilled in the art to include, but are not limited to, chemical chains, chemical compounds, carbohydrate chains, peptides, haptens, and the like. In various embodiments, linkers may include, but are not limited to, homobifunctional linkers and heterobifunctional linkers. Heterobifunctional linkers, well known to those skilled in the art, contain one end having a first reactive functionality to specifically link a first molecule, and an opposite end having a second reactive functionality to specifically link to a second molecule. Depending on such factors as the molecules to be linked, and the conditions in which the method of detection is performed, the linker may vary in length and composition for optimizing such properties as flexibility, stability, and resistance to certain chemical and/or temperature parameters. For example, short linkers of sufficient flexibility include, but are not limited to, linkers having from 2 to 10 carbon atoms (see for example U.S. Pat. No. 5,817,795). In particular examples, a linker may be a combination of streptavidin or avidin and biotin.

As used herein, the term "nanoparticle" refers to a particle having a maximum dimension of about 1000 nanometers (nm) in any direction, meaning that the particle does not have any dimension that exceeds 1000 nm. In some examples, a nanoparticle may have a maximum dimension of about 100 nm or less in any direction. An example of a nanoparticle is a quantum dot (QD), but other examples include iron oxide or gold nanoparticles.

As used herein, the terms "peptide," "protein," and "polypeptide" may all refer to a polymer of amino acids and/or amino acid analogs that are joined by peptide bonds or peptide bond mimetics. In one embodiment, a peptide may be an aptamer.

As used herein, the term "probe" refers to any molecule that specifically binds to a protein or nucleic acid sequence that is being targeted, and that may be identified (detected) so that the targets may then be detected. In particular examples, a probe may be a nanoparticle probe that is labeled with a specific binding agent for binding the nanoparticle to a target biomolecule, such as a particular protein, peptide, small molecule, or nucleic acid molecule. In certain embodiments, a probe may be identified by the color, or composition of a nanoparticle, or by the wavelength of light, such as a color of light, emitted by a nanoparticle (as in a quantum dot). In certain embodiments, the probe may include a nanoparticle conjugated to an antibody or other specific-binding molecule that binds to a target protein.

As used herein, the term "phosphoprotein" refers to a protein that is chemically bonded to a substance containing phosphoric acid (e.g., it is phosphorylated). Such proteins may be phosphorylated (e.g., activated) by members of the TK family in various examples. As used herein, TKs, proteins that may be phosphorylated by a TK, and proteins that appear downstream of a TK in a signal transduction pathway may all be referred to herein as "TK pathway proteins."

As used herein, the term "quantitating" or "quantifying" may refer to determining or measuring a quantity (such as a relative quantity) of a molecule, such as the quantity of a target biomolecule.

As used herein, the term "sample" refers to any quantity of a substance that includes targets (such as target biomolecules) that may be used in a method disclosed herein. In various embodiments, a sample may be a biological sample or may be extracted from a biological sample derived from humans, animals, plants, fungi, yeast, bacteria, tissue cultures, viral cultures, or combinations thereof. In particular examples of the disclosed compositions and methods, the biological sample may be a cellular suspension or a tissue section.

As used herein, the term "semiconductor nanocrystal" or "quantum dot" refers to a type of fluorescent label. Semiconductor crystalline nanospheres (also known as quantum dots), are engineered, inorganic, semiconductor nanocrystals that fluoresce stably and possess a uniform generally spherical surface area that may be chemically modified to attach biomolecules to them, such as a specific binding agent. Generally, semiconductor nanocrystals may be prepared with relative monodispersity (for example, with the diameter of the core varying approximately less than 10% between semiconductor nanocrystals in the preparation). Semiconductor nanocrystals known in the art have, for example, a core selected from the group consisting of CdSe, CdS, and CdTe (collectively referred to as "CdX"). These semiconductor nanocrystals may be used in place of organic fluorescent dyes as labels in immunoassays (as in U.S. Pat. No. 6,306,610) and as molecular beacons in nucleic acid assays (as in U.S. Pat. No. 6,500,622).

As used herein, the term "specific binding agent" refers to an agent that binds substantially only to a defined target. Thus, a protein-specific binding molecule may bind substantially only the specified protein. Examples include antibodies that bind to specific antigens, and nucleic acid molecules that hybridize to substantially identical complementary nucleic acid sequences under hybridization conditions of varying stringency (such as highly stringent conditions). Another example is a protein that specifically binds to a receptor (such as neurotrophin that specifically binds to a TrkA receptor expressed on the surface of certain neurons). Other examples of specific binding agents include aptamers.

As used herein, the term "target biomolecule" refers to a molecule of interest about which information is desired. A target biomolecule may be any molecule that is or once was part of a living organism. In several non-limiting examples, a target biomolecule may be a polypeptide, a nucleic acid, a ligand, or a small molecule. In one example, the information desired may be location of the biomolecule on or within a cell, such as a cell in a biological sample. In another example, the information desired may be the presence or absence of the biomolecule, for example in a sample, such as a biological sample.

As outlined above, the nanoparticle-based methods, apparatuses, and systems described herein may be used to detect, quantify, monitor, and/or characterize abnormally active TK signaling pathway proteins, such as those which may underlie tumorgenesis and tumor progression. In various embodiments, the nanoparticle-based technology disclosed herein may allow a very high degree of molecular sensitivity. For instance, in some embodiments, nanoparticle-based methods, systems, and apparatuses disclosed herein may allow identification of a single TK protein activation event in a single cell.

Additionally, the disclosed apparatuses, methods, and systems may provide subcellular resolution and a capacity to preserve tissue architecture in whole cell and tissue sections. In various embodiments, this high sensitivity may be helpful, given the labile nature and the low abundance of activated phosphoproteins in paraformaldehyde-fixed, paraffin-embedded tissue. In addition, embodiments disclosed herein may provide multiplexing capability, which may be used to elucidate the activation of multiple pathways in any one biological sample. Additionally, the disclosed probes they may be used with automated immunostainers in some embodiments, for instance for high-throughput and uniform immunohistochemical (IC) processing.

The following sections discuss several components of the disclosed methods and systems in greater detail.

Nanoparticles

Various embodiments disclosed herein may make use of a nanoparticle, such as a QD, coupled to a specific binding agent, such as an antibody probe specific for an activated (e.g., phosphorylated) TK signaling pathway protein, to identify and/or quantify the activated TK protein in a biological sample. In various embodiments, biological samples, such as tissue samples or cultured cells (or homogenates or lysates), or other biological fluids containing single or multiple target proteins, may be contacted with nanoparticle probes, for example semiconductor nanocrystals conjugated to specific binding agents (such as antibodies, ligands, peptides, or aptamers).

In various embodiments, the nanoparticles described herein may be discrete structures having dimensions less than or equal to about 1000 nm (for example, less than about 500 nm, less than about 400 nm, less than about 300 nm, less than about 200 nm, less than about 100 nm, less than about 50 nm, less than about 20 nm, less than about 10 nm, or even less than about 1 nm, for example 0.1 nm-1000 nm, such as 0.1-100 nm, 0.1-50 nm or 0.1-10 nm). In various embodiments, a nanoparticle may have three dimensions on the nanoscale. That is, the particle may be between 0.1 and 1000 nm in each spatial dimension, such as any integer or integer fraction between 0.1 and 1000 nm. For example, a particle may be between 0.1 and 100 nm in each spatial dimension, such as any integer or integer fraction between 0.1 and 100 nm.

In some embodiments, the nanoparticle may be a semiconductor nanocrystal, however in other embodiments, the nanoparticle may include any of various polymers, silica (including dye-doped silica), and metal oxides and metals, such as iron oxide and gold nanoparticles. Examples of methods of making gold nanoparticles are disclosed in U.S. Patent Publication 2005/0120174.

In various embodiments, nanoparticles used in the nanoparticle probes of the present disclosure may be of any shape (such as spherical, tubular, pyramidal, conical or cubical), and in particular examples the nanoparticles may be spherical. Without being bound by theory, it is believed that the spherical surface may provide a substantially smooth and predictably oriented surface for the attachment of specific binding agents, such as antibodies, with the attached agents extending substantially radially outwardly from the surface of the sphere.

In particular embodiments, the nanoparticle may be spaced from a specific binding agent (such as an agent that binds a target biomolecule, for example an antibody) by a linker. In various embodiments, the specific binding agent may be linked to the nanoparticle by a linker that spaces the binding agent slightly from the nanoparticle. As a result, in various embodiments, multiple specific binding agents may be distributed over the surface of the nanoparticle to form a three dimensional binding surface that efficiently interacts with target biomolecules, such as proteins.

In certain embodiments, the detectable nanoparticles may be semiconductor nanocrystals, also known as quantum dots (QD; QUANTUM DOTS™). In various embodiments, semiconductor nanocrystals may be nanoparticles having size-dependent optical and/or electrical properties. Thus, in various embodiments, when semiconductor nanocrystals are illuminated with a primary energy source, a secondary emission of energy may occurs of a frequency that corresponds to the bandgap of the semiconductor material used in the semiconductor nanocrystal.

In various embodiments, such as in quantum confined particles, the bandgap energy may be a function of the size and/or composition of the nanocrystal. For example, as the bandgap energy of such semiconductor nanocrystals varies with size, coating and/or material of the crystal, populations of these crystals may be produced that have a variety of spectral emission properties. Furthermore, in some embodiments, the intensity of the emission of a particular wavelength may be varied, thereby enabling the use of a variety of encoding schemes. In various embodiments, a spectral label defined by a combination of semiconductor nanocrystals with differing emission signals may be identified from the characteristics of the spectrum emitted by the label when the semiconductor nanocrystals are energized. Semiconductor nanocrystals with different spectral characteristics are described in U.S. Pat. No. 6,602,671.

In various embodiments, a mixed population of semiconductor nanocrystals of various sizes and/or compositions may be excited simultaneously using a single wavelength of light, and the detectable luminescence may be engineered to occur at a plurality of wavelengths. In various embodiments, the luminescent emission may be related to the size and/or the composition of the constituent semiconductor nanocrystals of the population. Furthermore, in various embodiments, semiconductor nanocrystals may be made highly luminescent through the use of a shell material that efficiently encapsulates the surface of the semiconductor nanocrystal core. For example, a "core/shell" semiconductor nanocrystal may have a high quantum efficiency and significantly improved photochemical stability. In some embodiments, the surface of the core/shell semiconductor nanocrystal may be modified to produce semiconductor nanocrystals that may be coupled to a variety of biological molecules or substrates by techniques described in, for example, Bruchez et al. *Science* 281:2013-2016, 1998; Chan et al. *Science* 281: 2016-2018, 1998; and U.S. Pat. No. 6,274,323.

In various embodiments, semiconductor nanocrystals may be used to detect or track a single target, such as a target biomolecule (for example, a protein expressed by a cell). Additionally, in various embodiments, a mixed population of semiconductor nanocrystals may be used for either simultaneous detection of multiple targets (such as, different target biomolecules) or to detect particular biomolecules and/or other items of interest, such as proteins, for example in a population of cells, such as cultured cells, a suspension of primary cells, or in tissue samples or sections, or disaggregated tissues or organs. For example, in various embodiments, compositions of semiconductor nanocrystals that include one or more particle size distributions having characteristic spectral emissions may be used to identify particular target biomolecules of interest. In certain examples, the semiconductor nanocrystals may be tuned to a desired wavelength to produce a characteristic spectral emission by changing the composition, size, or size distribution, of the semiconductor nanocrystal.

In some embodiments, the information encoded by the semiconductor nanocrystals may be spectroscopically decoded, thus providing the location and/or identity of the particular item or component of interest. In various embodiments, semiconductor nanocrystals for use in the disclosed methods and systems may be made using techniques known in the art. Additionally, examples of semiconductor nanocrystals suitable for use in the methods and systems disclosed herein may be available commercially, for example, from Life Technologies (Carlsbad, Calif.), Quantum Dot Corporation (Hayward, Ca), and Evident Technologies (Troy, N.Y.).

In various embodiments, the semiconductor nanocrystals used in the disclosed methods and systems may include nanocrystals of Group II-VI semiconductors, such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe, as well as mixed compositions thereof; as well as nanocrystals of Group M-V semiconductors such as GaAs, InGaAs, InP, and InAs, and mixed compositions thereof. The use of Group IV semiconductors such as germanium or silicon, or the use of organic semiconductors, also may be feasible under certain conditions. In various embodiments, the semiconductor nanocrystals also may include alloys that include two or more semiconductors selected from the group consisting of the above Group M-V compounds, Group II-VI compounds, Group IV elements, and/or combinations of the same. Formation of semiconductor nanocrystals of various compositions are disclosed in U.S. Pat. Nos. 6,927,069; 6,855,202; 6,689,338; 6,306,736; 6,225,198; 6,207,392; 6,048,616; 5,990,479; 5,690,807; 5,571,018; 5,505,928; and 5,262,357; as well as PCT Publication No. 99/26299.

In various embodiments, the semiconductor nanocrystals described herein may have a capability to absorb radiation over a broad wavelength band. This wavelength band may include the range from gamma radiation to microwave radiation in various embodiments. In addition, the semiconductor nanocrystals may have a capability to emit radiation within a narrow wavelength band of about 40 nm or less, for example, about 20 nm or less, thus permitting the simultaneous use of a plurality of differently colored semiconductor nanocrystal probes without overlap (or with a small amount of overlap) in wavelengths of emitted light when exposed to the same energy source. Both the absorption and emission properties of semiconductor nanocrystals may serve as advantages over dye molecules, which have narrow wavelength bands of absorption (such as about 30-50 nm) and broad wavelength bands of emission (such as about 100 nm) and broad tails of emission (such as another 100 nm) on the red side of the spectrum. Both of these properties of dyes impair the ability to use a plurality of differently colored dyes when exposed to the same energy source.

In various embodiments, the frequency or wavelength of the narrow wavelength band of light emitted from the semiconductor nanocrystal may be further selected according to the physical properties of the semiconductor nanocrystal. There are many alternatives for selectively manipulating the emission wavelength of semiconductor nanocrystals. In various embodiments, these alternatives may include varying the composition of the nanocrystal, and adding a plurality of shells around the core of the nanocrystal in the form of concentric shells. Thus, as one of ordinary skill in the art will realize, a particular composition of a semiconductor nanocrystal as listed above may be selected based upon the spectral region being monitored. For example, semiconductor nanocrystals that emit energy in the visible range include, but are not limited to, CdS, CdSe, CdTe, ZnSe, ZnTe, GaP, and GaAs. Semiconductor nanocrystals that emit energy in the near IR range include, but are not limited to, InP, InAs, InSb, PbS, and PbSe. Semiconductor nanocrystals that emit energy in the blue to near-ultraviolet include, but are not limited to, ZnS and GaN.

For example, in various embodiments, a nanocrystal composed of a 3 nm core of CdSe and a 2 nm thick shell of CdS may emit a narrow wavelength band of light with a peak intensity wavelength of 600 nm. In contrast, a nanocrystal composed of a 3 nm core of CdSe and a 2 nm thick shell of ZnS may emit a narrow wavelength band of light with a peak intensity wavelength of 560 nm. It should be noted that different wavelengths also may be obtained in multiple shell type semiconductor nanocrystals by respectively using different semiconductor nanocrystals in different shells, for example, by not using the same semiconductor nanocrystal in each of the plurality of concentric shells.

Additionally, in various embodiments, the emission spectra of semiconductor nanocrystals of the same composition may be tuned by varying the size of the particle with larger particles tending to emit at longer wavelengths. For example, semiconductor nanocrystals that emit at different wavelengths based on size (565 nm, 655 nm, 705 nm, or 800 nm emission wavelengths), which are suitable for use the methods disclosed herein, are available from Life Technologies (Carlsbad, Calif.).

Optionally, the emission of semiconductor nanocrystals may be enhanced in various embodiments by overcoating the particle with a material that has a higher bandgap energy than the semiconductor nanocrystal core. Suitable materials for overcoating are disclosed in U.S. Pat. No. 6,274,323. These and many other aspects of semiconductor nanocrystal design are disclosed in U.S. Pat. Nos. 5,990,479; 6,114,038; 6,207,392; 6,306,610; 6,500,622; 6,709,929; 6,914,256; and in U.S. Patent Publication 2003/0165951.

Specific Binding Agents

Various embodiments of the methods and systems disclosed herein involve nanoparticles, such as semiconductor nanocrystals, associated with a specific binding agent that may bind to a biomolecule of interest, such as a biomolecule expressed by a cell, for example a protein. Without limitation, nanoparticle conjugates may include any specific binding molecules (or molecular complexes), linked to a nanoparticle, that may interact with a biological target, to detect biological processes or reactions. In some embodiments, a specific binding molecule may physically interact with a biomolecule, for instance via a specific interaction. Such interactions may be, but are not limited to, covalent, non-covalent, hydrophobic, hydrophilic, electrostatic, Van der Waals, or magnetic interactions. In certain examples, the specific binding agent may be an antibody. However, one of skill in the art will recognize that the class of specific binding agents may include a wide variety of agents that are capable of interacting (binding) specifically with a biomolecule, such as a biomolecule expressed by a cell, such as receptors and receptor analogues, ligands, including small molecule ligands and other binding partners.

In various embodiments, nanoparticle conjugates, such as semiconductor nanocrystal conjugates, may be made using techniques known in the art. For example, moieties such as TOPO and TOP, generally used in the production of semiconductor nanocrystals, as well as other moieties, may be readily displaced and replaced with other functional moieties, including, but not limited to carboxylic acids, amines, aldehydes, and styrenes, for instance. One of ordinary skill in the art will realize that factors relevant to the success of a particular displacement reaction may include the concentration of the replacement moiety, temperature and reactivity. Thus, for the purposes of the present disclosure, any functional moiety may be utilized that is capable of displacing an existing functional moiety to provide a nanoparticle with a modified functionality for a specific use.

In various embodiments, the ability to utilize a general displacement reaction to modify selectively the surface functionality of the semiconductor nanocrystal enables functionalization for specific uses. For example, because detection of biomolecules and/or cells is often carried out in aqueous media (such as buffers and/or culture media), one example may use nanoparticles (such as, semiconductor nanocrystals) that are solubilized in water. In various embodiments, the outer layer of a water-soluble nanoparticle may include a compound having at least one linking moiety that attaches to the surface of the particle and that terminates in at least one hydrophilic moiety. In various embodiments, the linking and hydrophilic moieties may be spanned by a hydrophobic region sufficient to prevent charge transfer across the region.

In various embodiments, the hydrophobic region also may provide a "pseudo-hydrophobic" environment for the nanoparticle, and thereby may shield it from aqueous surroundings. Various examples of a hydrophilic moiety may include a polar or charged (positive or negative) group. In some embodiments, the polarity or charge of the group may provide hydrophilic interactions with water to provide stable solutions or suspensions of the nanoparticle. Exemplary hydrophilic groups may include polar groups such as hydroxides, amines, polyethers, such as polyethylene glycol and the like, as well as charged groups, such as carboxylates, sulfonates, phosphates, nitrates, ammonium salts, and the like. In some embodiments, a water-solubilizing layer may be found at the outer surface of the overcoating layer. Methods for rendering nanoparticles water-soluble are known in the art and described, for example, in International Publication No. WO 00/17655. In various embodiments, the affinity for the nanoparticle surface may promote coordination of the linking moiety to the nanoparticle outer surface, and the moiety with affinity for the aqueous medium may stabilizes the nanoparticle suspension. In some embodiments, a displacement reaction may be employed to modify the nanoparticle to improve the solubility in a particular organic solvent.

In various embodiments, nanoparticles, such as semiconductor nanocrystals, of varying sizes (such as, from about 1 nm to 1000 nm), composition, and/or size distribution may be conjugated to specific binding molecules that may bind specifically to a target biomolecule of interest. In various embodiments, the specific binding molecule may be selected based on its affinity for the particular target biomolecule of interest. In various embodiments, the affinity molecule may include any molecule capable of being linked to one or more nanoparticles that is also capable of specific recognition of a particular substance (such as a target biomolecule) of interest.

In general, any affinity molecule useful in the prior art in combination with a dye molecule to provide specific recognition of a detectable substance may find utility in the formation of the nanoparticle (such as semiconductor nanocrystal) probes. In various embodiments, such specific binding molecules may include, by way of example only, such classes of substances as monoclonal and polyclonal antibodies, nucleic acids (both monomelic and oligomeric), proteins, polysaccharides, and small molecules such as sugars, peptides, drugs, and ligands. Lists of such affinity molecules are available in the published literature such as, by way of example, the *Handbook of Fluorescent Probes and Research Chemicals* (sixth edition) by R. P. Haugland, available from Molecular Probes, Inc.

In certain examples, the specific binding molecule may be an antibody. More specifically, in various embodiments, the specific binding molecule may be derived from polyclonal or monoclonal antibody preparations, may be a human antibody, or may be a hybrid or chimeric antibody, such as a humanized antibody, an altered antibody, F(ab') 2 fragments, F(ab) fragments, Fv fragments, a single-domain antibody, a dimeric or trimeric antibody fragment construct, a minibody, or functional fragments thereof that bind to the biomolecule of interest.

In various embodiments, antibodies of use with the nanoparticle probes may be produced using standard procedures described in a number of texts, including Harlow and Lane (*Antibodies, A Laboratory Manual*, CSHL, New York, 1988). In various embodiments, the determination that a particular agent binds substantially only to the specified target biomolecule (such as a protein) may readily be made by using or adapting routine procedures. One suitable in vitro assay makes use of a Western blotting procedure. In various embodiments, Western blotting may be used to determine that a given binding agent binds substantially only to the desired target biomolecule.

In various embodiments, shorter fragments of antibodies may also serve as specific binding agents on the nanoparticles. For instance, Fabs, Fvs, and single-chain Fvs (SCFvs) that bind to a specified protein may be specific binding agents. These antibody fragments are described as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')2, the fragment of the antibody obtained by treating whole antibody with the enzyme pepsin without subsequent reduction; (4) F(ab')2, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

Optionally, in various embodiments, the specific binding agents may be attached to the nanoparticle via a linker, such as a streptavidin-biotin interaction. However, many different types of linking agents may alternatively be used to link the specific binding agent to the nanoparticle. Moreover, in some embodiments, the linking agent may be in the form of one or more linking agents linking one or more nanoparticles to one or more affinity molecules.

Alternatively, in some embodiments, two types of linking agents may be utilized. One or more of the first linking agents can be linked to one or more nanoparticles and also linked to one or more second linking agents. In various embodiments, the one or more second linking agents can be linked to one or more specific binding molecules and to one or more first linking agents.

One form in which the nanoparticle can be linked to an affinity molecule via a linking agent in various embodiments is by coating a semiconductor nanocrystal with a thin layer of glass, such as silica (SiO x where x=1-2), using a linking agent such as a substituted silane, such as 3-mercaptopropyl-trimethoxy silane to in the nanocrystal to the glass. The glass-coated semiconductor nanocrystal may then be further treated with a linking agent, such as an amine such as 3-aminopropyl-trimethoxysilane, which may function to link the glass-coated semiconductor nanocrystal to the affinity molecule. That is, in some embodiments, the glass-coated semiconductor nanocrystal may then be linked to the affinity molecule. In various embodiments, the original semiconductor nanocrystal compound also may be chemically modified after it has been made in order to link effectively to the affinity molecule. A number of references summarize the standard classes of chemistry which can be used to this end, in particular the *Handbook of Fluorescent Probes and Research Chemicals* (6th edition) by R. P. Haugland, available from Molecular Probes, Inc.; and *Bioconjugate Techniques* by Greg Hermanson, available from Academic Press, New York.

In various embodiment, when the semiconductor nanocrystal may be coated with a thin layer of glass, the glass, by way of example, may include a silica glass (SiO x where x=1-2), having a thickness ranging from about 0.5 nm to about 10 nm, or from about 0.5 nm to about 2 nm.

In various embodiments, the semiconductor nanocrystal may be coated with the coating of thin glass, such as silica, by first coating the nanocrystals with a surfactant such as tris-octyl-phosphine oxide, and then dissolving the surfactant-coated nanocrystals in a basic methanol solution of a linking agent, such as 3-mercaptopropyl-tri-methoxy silane, followed by partial hydrolysis which is followed by addition of a glass-affinity molecule linking agent such as aminopropyl trimethoxysilane which may link to the glass and serve to form a link with the affinity molecule.

These and many other techniques for linking specific binding agents to nanoparticles, such as semiconductor nanocrystals (including quantum dots), may be found in U.S. Pat. No. 5,990,479.

In various embodiments disclosed herein, antibodies may be made that will specifically bind only to an activated (e.g., phosphorylated) form of a certain protein, only to a non-activated (e.g., non-phosphorylated or dephosphorylated) form of a certain protein, or both. This may be of use when it is desirable to distinguish between an activated form of a protein and a non-activated for of the same protein, such as a TK pathway protein.

Target Biomolecules

As discussed above, in various embodiments, a specific binding agent may be conjugated or coupled to a nanoparticle to form a probe. In various embodiments, such probes may then be used to bind to and detect or quantify a target molecule of interest, such as a protein. Probe binding protocols, such as immunohistochemical protocols, are routine, and generally may include various fixation, permeabilization, blocking, incubating, and/or washing steps that may be adapted to suit the particular probe and target biomolecule, or the particular sample.

In various embodiments disclosed herein, the protein of interest may be a phosphoprotein, such as a TK pathway protein. As used herein, the term "kinase" encompasses a large family of enzymes that are responsible for catalyzing the transfer of a phosphoryl group from a nucleoside triphosphate donor, such as ATP, to an acceptor molecule. TKs catalyze the phosphorylation of tyrosine residues in proteins, and the phosphorylation of tyrosine residues in turn may cause a change in the function of the protein that they are contained in. As used herein, a "TK pathway protein" refers to any TK or any downstream protein in a TK signal transduction pathway. In some embodiments, the probe may target only the activated (e.g., phosphorylated) form of the target protein, only the non-activated (e.g., non-phosphorylated) form of the target protein, or both forms. Thus, in some embodiments, activated and non-activated forms of the same target protein may be separately quantitated, for instance, to determine what percentage of the population is activated.

Phosphorylation at tyrosine residues may control a wide range of properties in proteins, such as enzyme activity, subcellular localization, and interaction between molecules. Furthermore, TKs may function in many signal transduction cascades wherein extracellular signals are transmitted through the cell membrane to the cytoplasm and often to the nucleus where gene expression may be modified. Additionally, mutations may cause some TKs to become constitutively active, a nonstop functional state that may contribute to initiation or progression of cancer.

Approximately 2000 kinases have been identified, and more than 90 TKs have been found in the human genome. These are divided into two classes, receptor and non-receptor TKs. At present, 58 receptor tyrosine kinases (RTKs) are known, grouped into 20 subfamilies. They play pivotal roles in diverse cellular activities including growth, differentiation, metabolism, adhesion, motility, death. Generally speaking, RTKs have an extracellular domain, which is able to bind a specific ligand, a transmembrane domain, and an intracellular catalytic domain, which is able to bind and phosphorylate selected substrates. Binding of a ligand to the extracellular region causes a series of structural rearrangements in the RTK that lead to its enzymatic activation. These structural changes trigger a cascade of events through phosphorylation of intracellular proteins that ultimately transmit ("transduce") the extracellular signal to the nucleus, causing changes in gene expression. Many RTKs are involved in oncogenesis, either by gene mutation, or chromosome translocation, or simply by over-expression. In each case, the result may be a hyper-active kinase that confers an aberrant, ligand-independent, non-regulated growth stimulus to the cancer cells.

In humans, 32 cytoplasmic TKs have been identified to date. The first non-receptor tyrosine kinase identified was the v-src oncogenic protein. Most animal cells contain one or more members of the Src family of tyrosine kinases, and the mutated v-src gene has lost the normal built-in inhibition of enzyme activity that is characteristic of cellular SRC (c-src) genes. SRC family members have been found to regulate many cellular processes. For example, the T-cell antigen receptor leads to intracellular signalling by activation of Lck and Fyn, two proteins that are structurally similar to Src.

TKs are of clinical significance at least in part because of their implications in the treatment of cancer. For instance, a mutation that causes certain TKs to be constitutively active has been associated with several cancers, and the anti-cancer drug Imatinib (GLEEVEC™) works by binding the catalytic cleft of these TKs, inhibiting their activity.

In addition to its role in cancer, enhanced TK activity also has been implicated in deranged cell division, diseases related to local inflammation, such as atherosclerosis and psoriasis, and diseases involving systemic inflammation, such as sepsis and septic shock. A number of viruses target TKs, such as the polyoma virus and the Rous sarcoma virus, a retrovirus that causes sarcoma in chickens. TKs that are encoded by the Rous sarcoma virus may cause cellular transformation, and may be referred to as oncoproteins.

In addition, overactive TKs may lead to non-small cell lung cancer (e.g., due to over-active EGF receptor), chronic myeloid leukemia (CML) (e.g., due to constitutively activated BCR-ABL), or gastrointestinal stromal tumors (GIST) (e.g., due to a mutation in c-kit). Specific examples of human proteins containing a TK domain include, but are not limited to: AATK; ABL1; ABL2; ALK; AXL; BLK; BMX; BTK; CSF1R; CSK; DDR1; DDR2; EGFR; EPHA1; EPHA2; EPHA3; EPHA4; EPHA5; EPHA6; EPHA7; EPHA8; EPHA10; EPHB1; EPHB2; EPHB3; EPHB4; EPHB6; ERBB2; ERBB3; ERBB4; FER; FES; FGFR1; FGFR2; FGFR3; FGFR4; FGR; FLT1; FLT3; FLT4; FRK; FYN; GSG2; HCK; IGF1R; ILK; INSR; INSRR; IRAK4; ITK; JAK1; JAK2; JAK3; KDR; KIT; KSR1; LCK; LMTK2; LMTK3; LTK; LYN; MATK; MERTK; MET; MLTK; MST1R; MUSK; NPR1; NTRK1; NTRK2; NTRK3; PDGFRA; PDGFRB; PLK4; PTK2; PTK2B; PTK6; PTK7; RET; ROR1; ROR2; ROS1; RYK; SGK493; SRC; SRMS; STYK1; SYK; TEC; TEK; TEX14; TIE1; TNK1; TNK2; TNNI3K; TXK; TYK2; TYRO3; YES1; and ZAP70. In specific embodiments disclosed herein, a TK target protein may be a KIT TKR signaling pathway protein, an ABL TK signaling pathway protein, or a PI3 TK signaling pathway protein. In specific embodiments, the TK target protein may be a phosphorylated or unphosphorylated form of Abl, Akt, Crkl, ERK, STAT3, or STAT5.

Nanoparticle Detection

In various embodiments, semiconductor nanocrystals bound to the biomolecular constituent of interest may be qualitatively or quantitatively detected under illumination, such as UV-illumination, using available detection technologies, such as fluorescence scanners and/or digital cameras. If desired, in various embodiments, different specific binding agents conjugated to different semiconductor nanocrystals with different spectral properties may be used to detect different cellular components in the same sample.

In various embodiments, separate populations of semiconductor nanocrystals may be produced that are identifiable based on their different spectral characteristics. In the context of the methods disclosed herein, separate populations of semiconductor nanocrystals with different emission spectra may be used to identify different biomolecules, for example, different proteins, or different forms of the same protein, such as a mutant protein and a wild-type protein, or an activated (e.g., phosphorylated) protein and its non-activated counterpart. For example, each of two or more different populations of semiconductor nanocrystals to which specific binding agents are attached may be contacted with a biological sample, and the characteristic emissions may be observed as colors (if in the visible region of the spectrum) or may be decoded to provide information about the particular wavelength at which the discrete transition is observed. Likewise, in various embodiments, for semiconductor nanocrystals producing emissions in the infrared or ultraviolet regions, the characteristic wavelengths at which the discrete optical transitions occur may provide information about the identity of the particular semiconductor nanocrystal, and hence about the identity of biomolecule of interest.

In various embodiments, the color of light produced by a particular size, size distribution, and/or composition of a semiconductor nanocrystal may be readily calculated or measured by methods which will be apparent to those skilled in the art. As an example of these measurement techniques, the bandgaps for nanocrystals of CdSe of sizes ranging from 12 A to 115 A are given in Murray et al., *J. Am. Chem. Soc.* 115:8706, 1993. Thus, these techniques may allow ready calculation of an appropriate size, size distribution, and/or composition of semiconductor nanocrystals and choice of excitation light source to produce a nanocrystal capable of emitting light device of any desired wavelength.

Methods and devices for eliciting and detecting emissions from semiconductor nanocrystals are well known in the art. In brief, a light source typically in the blue or UV range that emits light at a wavelength shorter than the wavelength to be detected may be used to elicit an emission by the semiconductor nanocrystals. Numerous such light sources (and devices incorporating such light sources) are known in the art, including without limitation: deuterium lamps and xenon lamps equipped with filters, continuous or tunable gas lasers, such as argon ion, HeCd lasers; solid state diode lasers (for example, GaN, GaAs lasers); YAG and YLF lasers; and pulsed lasers. In various embodiments, the emissions of semiconductor nanocrystals may be similarly detected using known devices and methods, including without limitation, spectral and hyperspectral imaging systems, such as those disclosed in U.S. Pat. No. 6,759,235. Optionally, the emissions may be passed through one or more filters or prisms prior to detection.

In various embodiments, when stimulated with broadband excitation, these particles may exhibit extended photostability. In some examples, the stable fluorescent emission of semiconductor nanocrystals, unlike traditional organic dyes (such as rhodamine or FITC), may allow free colloidal suspensions of semiconductor nanocrystals to be used to successfully attach and bind specific proteins to cells, and to identify and label proteins and cells living months after attachment without significant bleaching (Chan et al., *Science*, 1998. 281: 2016-8). In various embodiments, the simultaneous multicolor wavelength, such as multicolor, identification of semiconductor nanocrystals may permit rapid identification of probes without requiring fixation of the cells. Additionally, in some embodiments, the wavelength of light emitted, such as the color of light, may be tuned based on size of the nanoparticle.

Various embodiments may enable the detection of multiple biomolecules of interest in a single sample. In various embodiments, this method may include contacting a sample, such as a biological sample, that contains or is suspected of containing a plurality of different biomolecules of interest with a different nanoparticle probe specific for each different biomolecule of interest, wherein the different nanoparticle probes include different detectable nanoparticles. In various embodiments, the formation of a complex between the target biomolecules of interest and the different nanoparticle probes specific for each different biomolecule of interest may effectively label the target biomolecules of interest in the sample. In various embodiments, the nanoparticles may be detected, such that detection of the nanoparticle detects the different target biomolecules of interest in the electrophoresed sample, for example relative to a different molecular weight. In some embodiments, each different biomolecule of interest may be labeled with a nanoparticle probe having a defined physical characteristic different from the other nanoparticle probes, and the different biomolecules of interest may be separated by the physical characteristic of the nanoparticle probe.

In some embodiments, the physical characteristic of the nanoparticle probes may be the size of the nanoparticle probes. In some embodiments, the physical characteristic of the nanoparticle probes may be the mass of the nanoparticle probes, whereas in other embodiments, the physical characteristic of the nanoparticle probes may be the charge of the nanoparticle probes. In some embodiments, each of the different detectable nanoparticle probes may include a specific binding agent that may specifically bind each different biomolecule of interest. In some embodiments, each of the different detectable nanoparticles may include a different semiconductor nanocrystal that may emit a characteristic detectable electromagnetic spectrum distinct from the other semiconductor nanocrystals. In some embodiments, the characteristic emission spectra from the different semiconductor nanocrystals may be light, and the different biomolecules of interest may be detected by detecting different wavelengths of light, such as colors of light. In some embodiments, the presence of different biomolecules of interest may be detected by the kinetic fluctuations in the electromagnetic emission of the semiconductor nanocrystal (e.g., blinking).

Image Acquisition and Quantitation/Analysis

In various embodiments, various methods, apparatuses, and devices may be used to quantitate the nanoparticle signal, and therefore the target protein. In some embodiments, substantially automated detection and/or analysis methods may be used to detect and/or quantitate phosphoproteins present at trace concentrations in complex, heterogeneous tissues and biofluid samples. In various embodiments, the apparatuses, systems, and methods described herein may be useful for detecting phosphoproteins such as TK pathway proteins in small populations of cells. Such detection of low numbers of phosphoproteins in small numbers of cells may be useful in certain applications, such as in a solid tumor or cell biopsy, where only small numbers of cells may be available.

Figure 1B:
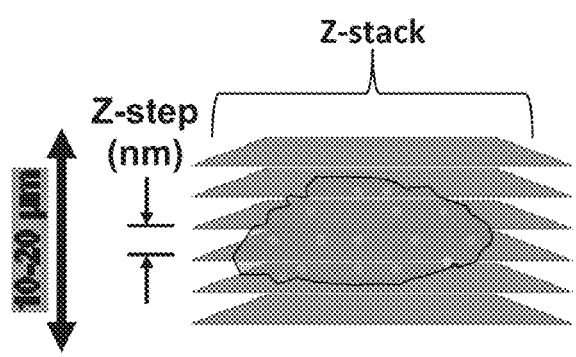
Figure 1B:
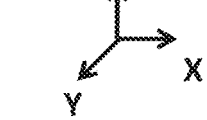

FIGS. 1A-1B illustrate a schematic of a 3-D imaging system (FIG. 1A) and a schematic of Z-stack imaging (FIG. 1B), in accordance with various embodiments. As illustrated in FIG. 1A, an embodiment of a system 100 for automated detection and counting of biomolecules may include a microscope 102, a computer 104, a camera 106, an automated XYZ stage 108, a drive unit 110, a DAQ board 112, and a user interface 114. In various embodiments, microscope 102 may include one or more microscope objectives, one or more filter cubes, and a light source. In various embodiments, a sample containing the cells to be imaged may be placed on automated stage 108. In various embodiments, the sample may include whole cells, and may be a cell or tissue sample, such as fresh, frozen, or fixed cells or tissue. In various embodiments, the sample may sit on a transparent base material, such as a glass or plastic slide or dish.

In various embodiments, computer 104 may be coupled to camera 106, stage 108, drive unit 110, DAQ board 112, user interface 114, the objectives, the filter cubes, and/or the light source, for instance through electrical cables or wireless communication. In operation, in various embodiments, a user may turn on the light source, which may emit an excitation light. The excitation light may be at a first wavelength and may encounter the filter cube(s), which may contain a dichroic mirror passing certain wavelengths and reflecting others. In various embodiments, the filter cube(s) may reflect desired wavelengths of the excitation light through one of the objectives to stage 108. In various embodiments, the objectives may have any level of magnification, but a typical magnification may be between about 63X and about 100X.

In various embodiments, the excitation light may cause the nanoparticles specifically bound to phosphoprotein in the sample to fluoresce, which may produce an emission light. In various embodiments, the emission light may then pass through the objective, into the filter cube(s), and to camera 106. In various embodiments, the emission light may be at a second wavelength, different than the excitation light, and the filter cube(s) may pass light at the second wavelength to camera 106. In various embodiments, camera 106 may capture an image of the excitation light in response to a control signal from computer 104, for instance via DAQ board 112. In various embodiments, XYZ stage 108 may then be controlled by computer 104, for example via drive unit 110, to position the sample at a new X-Y-Z position and the process may be repeated. In various embodiments, a plurality of images may be captured at different levels along the Z axis in order to generate a Z stack, as illustrated in FIG. 1B.

FIGS. 2A-2E illustrate a schematic of one embodiment of a method of interactive cell segmentation and counting of QDs in 3D. In various embodiments, this method may prevent over-counting or under-counting of QDs that overlay each other along the Z-axis, and may permit 3D spatial reconstruction of the location of individual QDs within a cell or tissue section. As shown in several panels in FIG. 2A, the DIC image and the corresponding Z-Stack (panel 224) may be loaded using the user interface (panel 222). In the illustrated example, a sample image is shown that has QD-565 labeled human leukocytes, and Z-stacks were obtained at an interstice distance of 275 nm. In the illustrated example, the total Z-depth is 10 μm (~37 slices).

Figure 2A:
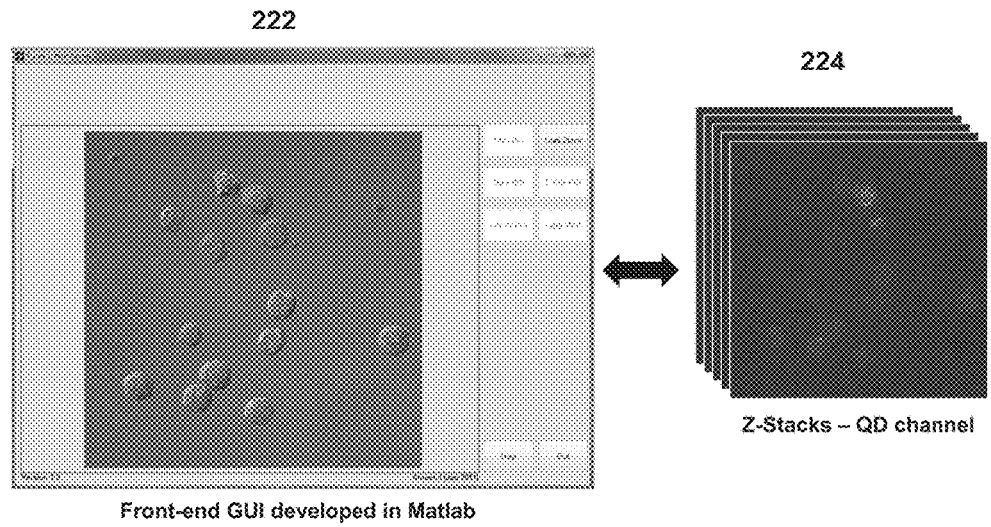
FIGS. 2A-2E illustrate schematic diagrams of the steps involved in interactive cell segmentation and counting of QDs in 3-D, including loading the DIC image (FIG. 2A), image processing (FIG. 2B), selection of individual cells (FIG. 2C), application of masks to the Z-stacks (FIG. 2D), and image filtering and thresholding (FIG. 2E), in accordance with various embodiments.
Figure 2B:
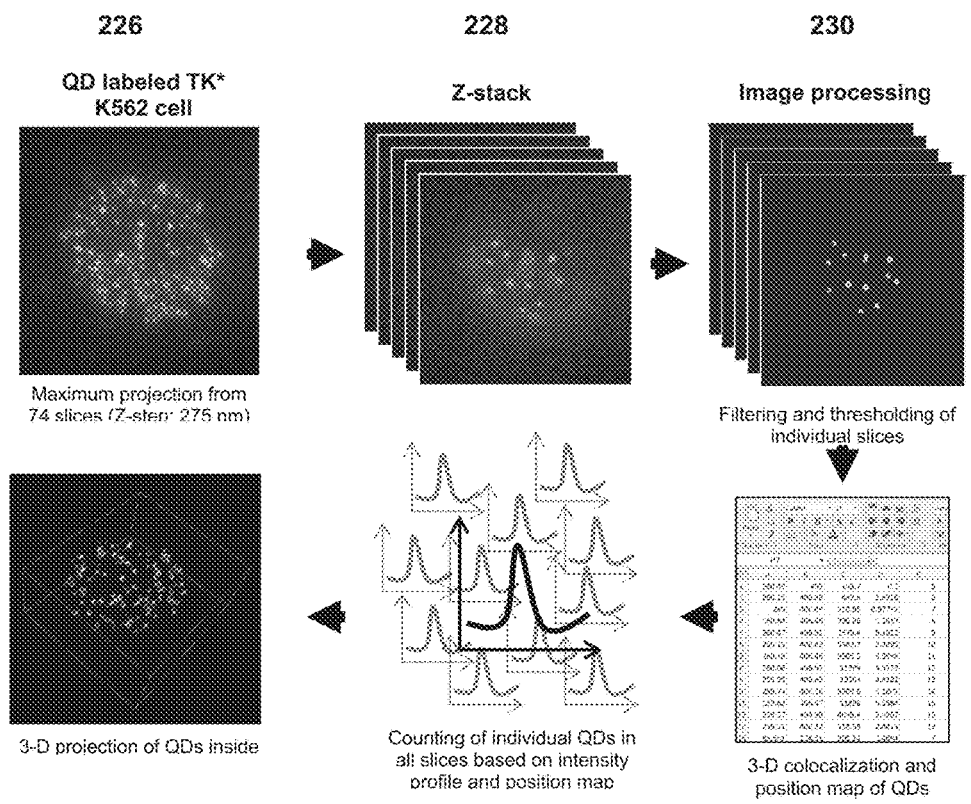

FIG. 2B illustrates an example of a portion of an image analysis process, wherein an image of a QD labeled K562 cell (panel 226) is shown as a Z stack of 74 optical sections (panel 228) which may be individually filtered and thresholded (panel 230) and the fluorescent QDs may be converted to an XYZ coordinate map (panel 232). The individual QDs in all slices may then be counted based on intensity profile and position map (panel 234), and a 3D projection (panel 236) of the position of each QD within the cell may be created.

Figure 2C:
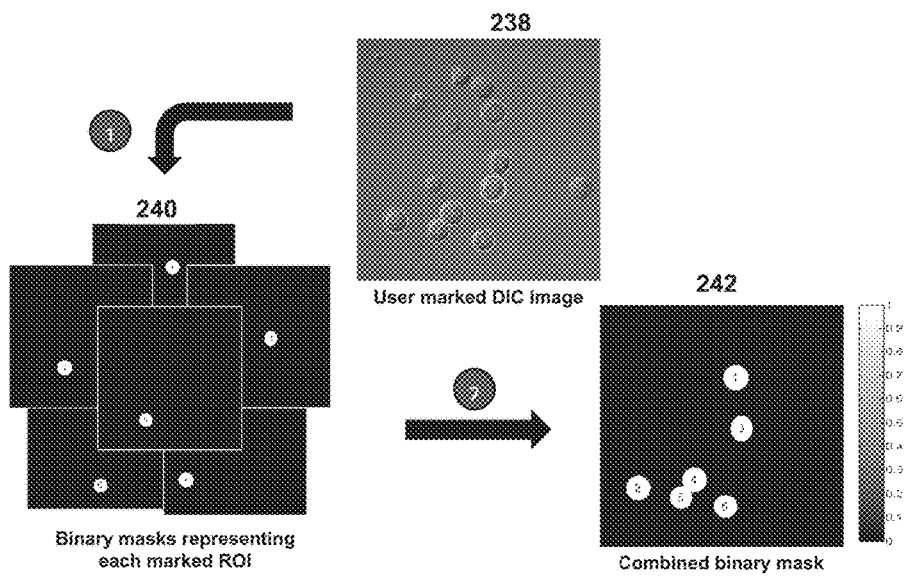
Figure 2D:
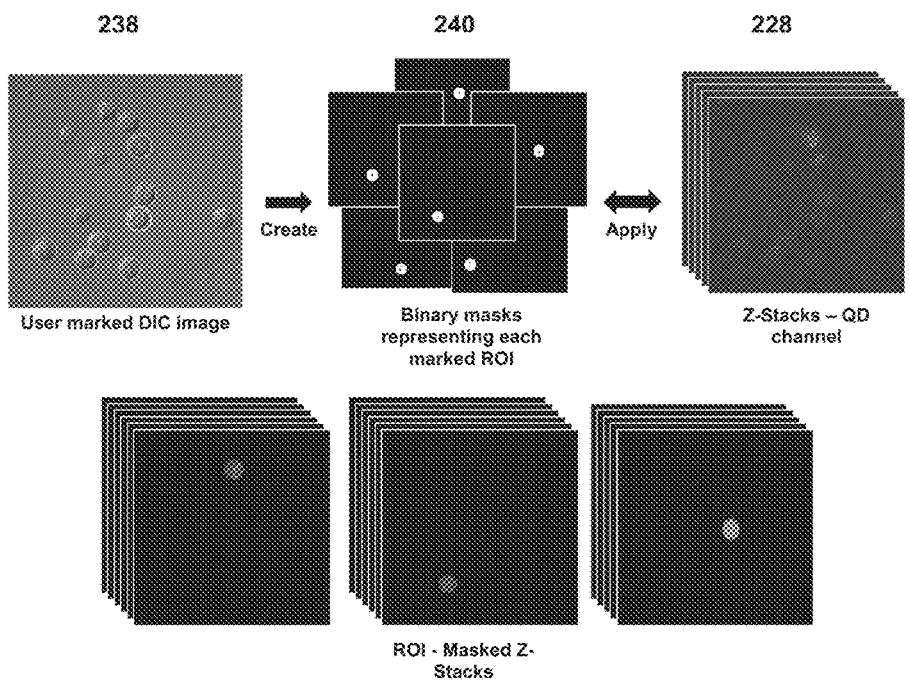

FIG. 2C illustrates the application of masks to the Z-stacks. In the illustrated embodiment, in the DIC image, individual cells of interest may be selected and marked using the interactive region of interest (ROI) tool (panel 238). In various embodiments, the ROI may be stretched or shrunk depending upon the morphology of the cell. In various embodiments, in order to count the QDs in individual cells, cell segmentation may be performed by creating a binary mask for each ROI marked in the DIC (panel 240), and creating a combined binary mask image (panel 242), in accordance with various embodiments. This process is illustrated in further detail in FIG. 2D, where the user marked DIC image (panel 238) and the Z-stacks (panel 228) may be combined to create a binary mask image (panel 240), in accordance with various embodiments. In various embodiments, these may yield the binary masked Z-stacks illustrated in panel 224, when individual masks are separately applied to the original Z-stacks to isolate the QD channel data for individual marked ROI's (user marked cells).

Figure 2E:
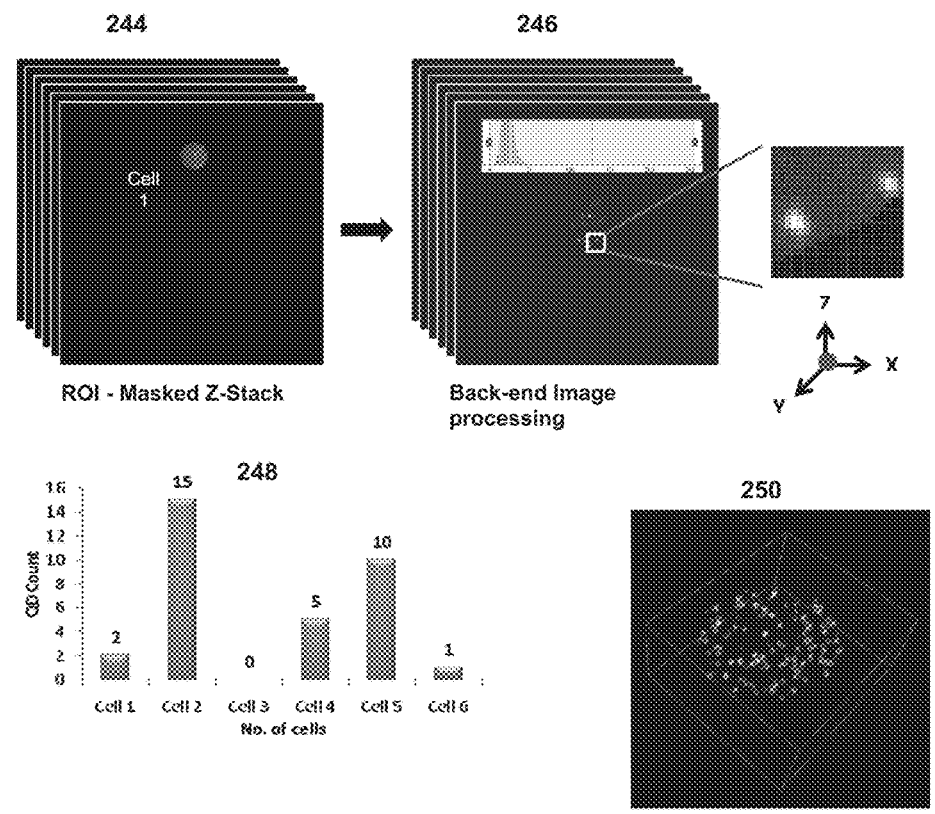

As illustrated in FIG. 2E, in various embodiments, for each set of masked Z-stacks (panel 244), image filtering and thresholding may be performed (panel 246), for instance to identify and mark individual QDs based on pixel intensity and create an overall 3D position map of the QDs in all the slices (panel 250). In various embodiments, this position map data may be then used for quantification (panel 248) and 3D visualization (panel 250) of the distribution of QD's inside cells.

Figure 7:
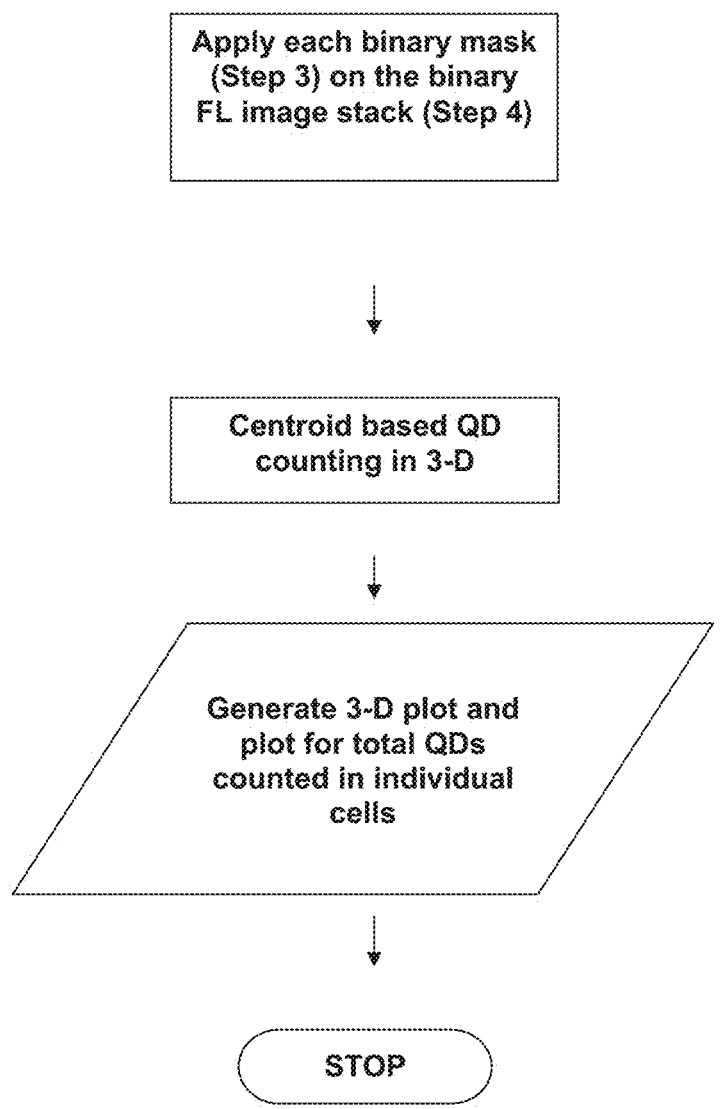
FIG. 7 is a flow chart illustrating the method shown in FIGS. 2A-2E, in accordance with various embodiments.

FIG. 7 is a flow chart illustrating the steps involved in the method illustrated in FIGS. 2A-2E. This specific, non-limiting example includes a MATLAB-based algorithm for interactive cell/tissue segmentation and counting of QDs in 3D space. In this example, a DIC image and FL image stack are loaded, and an ROI is selected and its position recorded. Separate binary masks are then generated for each ROI, and a threshold is set for the FL image stack. Each binary mask is then applied to the binary FL image stack, and centroid-based QD counting is carried out in 3D, A 3D plot for total QDs counted in individual cells is then generated.

Figure 8G:
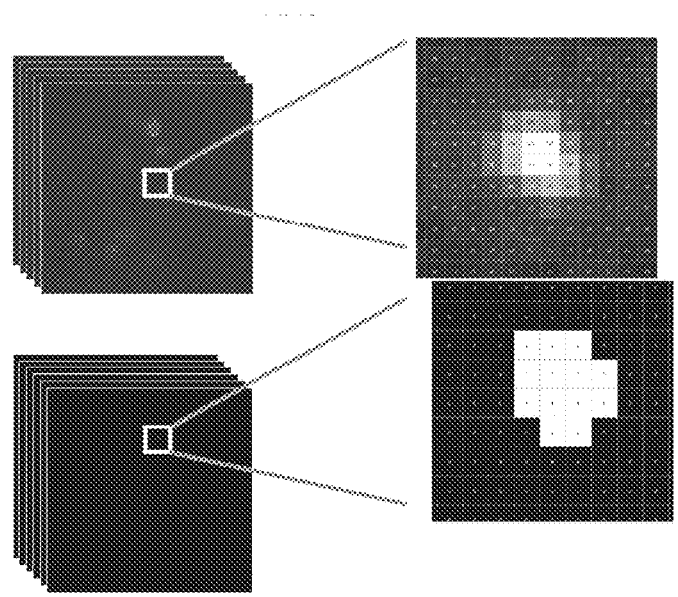

In another embodiment, a similar example of a method of QD quantitation in a cell or tissue sample is presented in greater detail in FIGS. 8A-8J. As illustrated in FIGS. 8A-8J, in some embodiments, a user interactive dialog box may prompt the user to load a Differential Interference Contrast (DIC) image (FIG. 8A) and the corresponding fluorescence (FL) image stack (FIG. 8B) for the cell/tissue sample. In the illustrated example, the DIC image includes a single 2D image representing the actual morphology of the cells in a given field-of-view. In the illustrated example, the FL image includes a sequence of several 2D images obtained in the axial Z direction, together referred to as a 3D image stack. As illustrated, in this example of the FL image stack, the fluorescence channel may represent the distribution of QDs inside the sample in 3D space (FIG. 8C).

In various embodiments, the DIC image may act as a template on which the user may interactively select a region-of-interest (ROI) and record its position in real time (FIG. 8D). In the illustrated example, for image segmentation, the algorithm may use this position information to create a binary mask for each of the marked ROIs (FIG. 8E). As illustrated in FIG. 8F, in various embodiments, a binary mask may be an image matrix consisting of 0's and 1's, where '0' represents a black pixel and '1' represents a white pixel.

As illustrated in FIG. 8G, in particular examples, the FL image stack may be represented by 0-255 gray levels, where 0 presents a black pixel and 255 presents a white pixel. In some embodiments, the user may interactively select a global threshold value for the FL image stack in the range of 0-255 to create a binary FL image stack. In particular embodiments, the threshold value may be selected such that the algorithm retains only the bright pixels for further processing. In various embodiments, all the pixel values below the set threshold may be assigned a pixel value of '0' (e.g., background) and pixel values above the set threshold may be assigned a value of '1' (e.g., QDs).

Figure 8H:
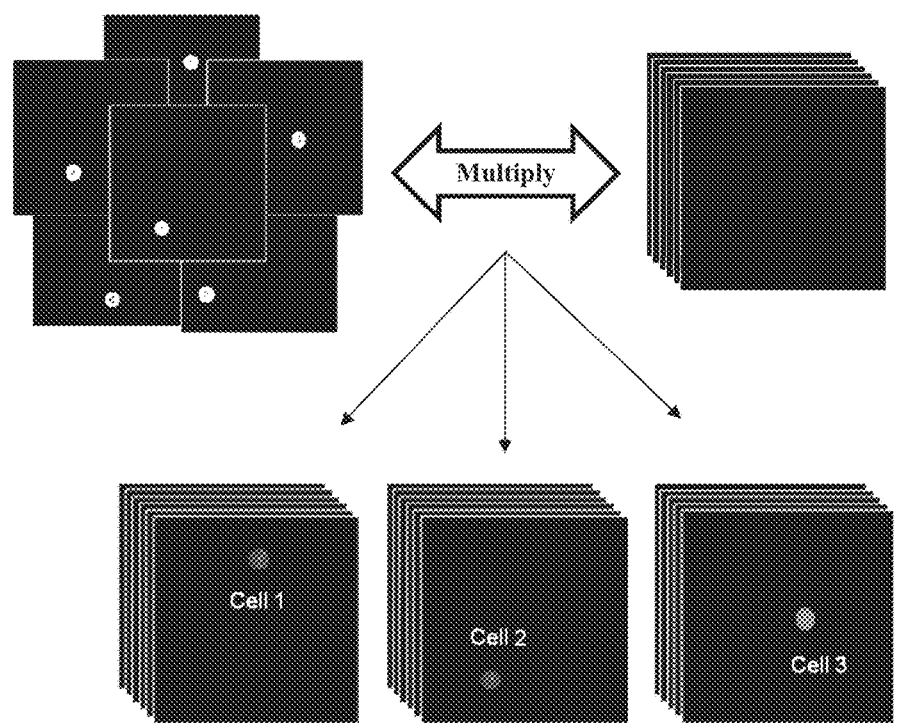

As illustrated in FIG. 8H, each of the binary masks obtained as shown in FIG. 8F may be implicitly multiplied with the threshold binary FL image stack obtained as shown in FIG. 8G. Without being bound by theory, this step may be important in isolating the FL channel data corresponding to each ROI (cell) selected by the user as shown in FIG. 8D. In various embodiments, the 3D data set thus generated may correspond to the amount of the QD probe in each individual cell.

In some embodiments, to count QDs in an image stack, the algorithm may rely on logic based on pixel connectivity in 3D. In some embodiments, processing may start from the brightest pixel in the image and spread through rest of the image based on the connectivity of pixels. In particular embodiments, a set of such connected pixels may be called an 'object' or a 'connected component,' and in the illustrated embodiment, this algorithm used 26-connectivity, and pixels were determined to be connected if their faces, edges or corners touched (e.g., 6 faces+12 edges+8 corners).

Figure 8I:
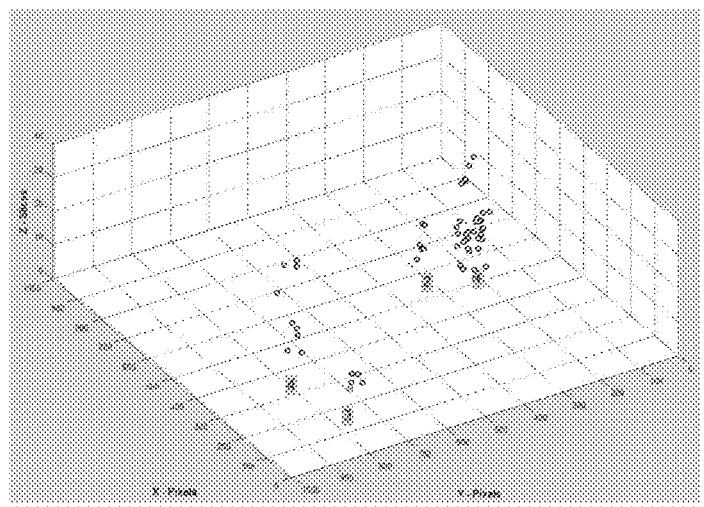

As illustrated in FIG. 8I, in some embodiments, the algorithm may then analyze the individual image stacks for each cell based on the defined connectivity and calculate the centre of mass of the region (centroid). In some embodiments, this centroid information may account for QD present in mulitple Z-sections. In particular embodiments, bright pixels that are represented by QDs in multiple z-sections may be connected in 3D and assigned as a single 'object' with a unique centroid. Thus, in various embodiments, the number of centroids thus calculated may correspond to the number of unique 'obejcts' counted in the image.

Figure 8J:
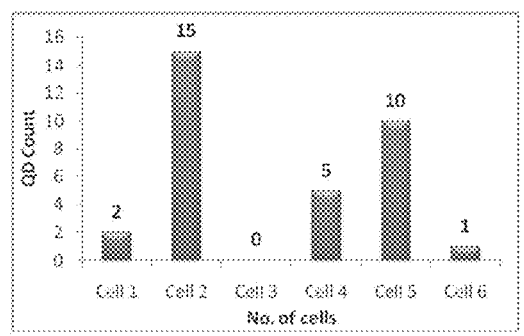

As illustrated in FIG. 8J, in some embodiments, the centroid data may represent the position map of the QDs in 3D space for individual cells. Thus, in some embodiments, the final output of the algorithm may be a plot of total QDs counted in each cell. In various embodiments, the automated quantification described herein may allows for counting of discrete groups of nanoparticle probes (e.g., any number from 2-100, such as 5, 10, 50, etc.) or single nanoparticle probes.

Kits

Aspects of this disclosure may relate to kits for the detection/quantitation of a target biomolecule of interest. In various embodiments, nanoparticle probes may be supplied in the form of a kit for use in carrying out the disclosed methods. In such a kit, an appropriate amount of one or more nanoparticle probes may be provided in one or more containers. In some embodiments, a nanoparticle probe may be provided suspended in an aqueous solution or as a freeze-dried or lyophilized powder, for instance. In various embodiments, the nanoparticle probes may be supplied in any conventional container that is capable of holding the supplied form, for instance, microfuge tubes, ampoules, or bottles. In some embodiments, the kit may include equipment, reagents, and/or instructions for labeling and/or detecting the target biomolecules of interest. In various embodiments, the amount of the nanoparticle probes supplied in the kit may be any appropriate amount, and may depend on the target market to which the product is directed. For instance, if the kit is adapted for research or clinical use, the amount of each nanoparticle probe may be an amount sufficient for several labeling procedures.

In certain embodiments, the nanoparticle probe may include a semiconductor crystal, such as a quantum dot. In some embodiments, the nanoparticle probe may include a specific binding agent (such as an antibody, a ligand, an aptamer, or a peptide) that specifically binds the target biomolecule of interest, such as a TK pathway protein. In some embodiments, the detectable nanoparticle may be conjugated directly to the specific binding agent, whereias in other embodiments, a linker may be used to link the detectable nanoparticle and the specific binding agent. In specific embodiments, the linker may be streptavidin, avidin, biotin, or a combination thereof. In some examples, a nanoparticle probe may be conjugated to streptavidin, avidin, or biotin such that the nanoparticle probe may be attached to a specific binding agent that is conjugated to streptavidin, avidin, or biotin.

The following examples are provided to illustrate particular features of certain embodiments. However, the particular features described below should not be construed as limitations on the scope of the invention, but rather as examples from which equivalents will be recognized by those of ordinary skill in the art.

EXAMPLES

Example 1

Immobilization of Leukocytes and Other Cells for QD Labeling/Imaging

This example illustrates a method for immobilizing leukocytes and other cells for QD labeling and/or imaging. In various embodiments, leukocytes (e.g., human white blood cells) may be 'slippery' cells that may not adhere well to glass or plastic surfaces. Thus, in various embodiments, in order to perform QD probe assays, the cells may be fixed and immobilized (e.g., cross linked) onto aminopropyltriethoxysilane-(APTES) coated cover glasses in presence of 1.6% paraformaldehyde (PFA), followed by mild centrifugation of cells at 60 RCF for 5 minutes, and subsequent incubation at 37° C. for 10-20 minutes. Introduction of the APTES chemistry on the coverglass may drastically increase its binding capacity to cellular membrane proteins, and the chemical cross linking may be further enhanced by the presence of PFA (or gluteraldehyde). In various embodiments, these optimized cell binding techniques may improve the immobilization of leukocytes to withstand QD probe treatments and washing conditions with minimum cell loss during the assay.

In various embodiments, the technique of PFA-mediated cell immobilization to APTES coated glass surfaces may make it feasible to conduct QD probe assays with as few as 5,000-10,000 cells per assay. Towards this end (e.g., achieving such lower cell volume assays), the cell binding surface area may be further optimized to as small as 10-15 $mm^2$ of the coverglass in an assay chamber. In some examples, the ability to perform QD probe assays with low cellular sampling sizes may be advantageous, especially when assessing phosphoprotein levels in limited sample types, such as circulating tumor cells. Conventional protein assays such as Western blot, ELISA, and microarrays typically require 0.5-1 M cells per assay. Furthermore, the optimized QD probe assay techniques disclosed herein may allow the use of entire cells without any protein extraction procedures, which otherwise is typically required in conventional protein quantification assays.

Example 2

Treatment of Cells for Enhancement of Assay Specificity and Sensitivity

This example illustrates methods of optimization for increasing specificity and sensitivity in a QD assay. In various embodiments, antibody-QD probe treatments may be optimized to deliver appropriate amounts of the QD probe into the cells. In various embodiments, high assay sensitivity and specificity may be achieved by optimizing the assay reagent concentrations using serial titration techniques. The probe binding and cell washing conditions may be further optimized by using an incubation temperature of about 37° C. to increase the probe specificity in some examples.

In various embodiments, the reagent treatments and washing conditions may be optimized by gentle reagent delivery techniques at low flow rates, ensuring the least physical disturbances of immobilized cells on the coverglass. In particular examples, gentle reagent delivery may be performed by either controlled pipetting or liquid pumping techniques at flow rates not exceeding about 10 µL/sec. In some examples, reagent delivery may be further optimized so that the liquids are introduced along the side walls of the assay chamber, thus avoiding pipetting directly onto the cells.

In various embodiments, such optimized methods of reagent delivery mechanisms may enable higher assay specificity by reducing nonspecific binding, may increase assay sensitivity by increasing the signal to noise ratio, and may minimize loss of cell samples during the assay procedures. In some embodiments, low levels of non-specific binding of QD probes may be achieved in the range of <10 QDs for K562 cells, and <5 QDs for WBCs, where as the signal intensity can reach the range of hundreds of QDs per cell or more in positive samples using similar assay conditions.

Example 3

QD Probe Assay for STAT5*

This example describes the visualization of activated TK protein STAT5* in whole cells, and demonstrates that a QD probe assay, properly optimized, may be used to detect and quantify target phosphoproteins at molecular-level resolution in single cells and tissues. Briefly; control tumor cells and tumor cells treated with Gleevec™ were processed (fixing, permeabilization, blocking, washing, etc.) to specifically bind optimized concentrations of QD-anti-STAT5* antibody probes to STAT5* protein kinase. After washing, the cells were imaged in multiple slices using the imaging techniques described above, covering the entire 3D space of the cells. QD probe bound to the cells was then compiled and projected on the cell for quantification.

Figures 9A, 9B, 9C:
FIGS. 9A-9C are digital images of QD-STAT5* labeling of tumor cells (FIG. 9A), tumor cells treated with Gleevec™ (FIG. 9B), and control cells with antibody omitted (FIG. 9C), in accordance with various embodiments.

As shown in FIGS. 9A-9C, control (untreated) tumor cells (FIG. 9A) showed a high level of STAT5* binding, whereas cells treated with Gleevec™ (FIG. 9B) showed a marked decrease in STAT5* activation. FIG. 9C shows the negative control (antibody omitted), illustrating the specificity of the QD probe.

Example 4

Quantification of the Effectiveness of Dasatanib in Cancer Cell Lines

Figures 3A, 3B, 3C:
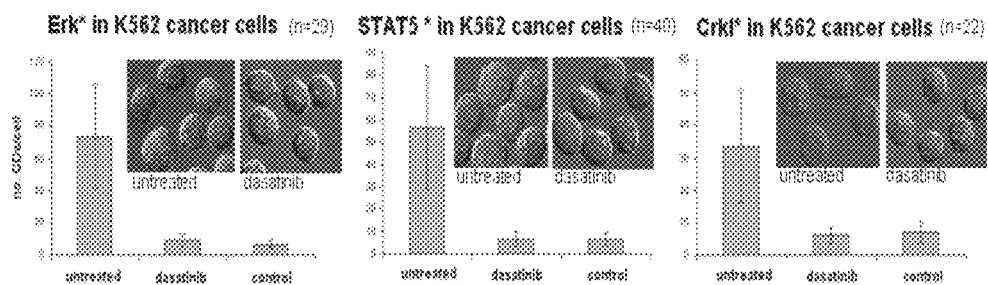
FIGS. 3A-3C illustrate digital images of QD-Erk* (FIG. 3A), QD-STAT5* (FIG. 3B), and QD-Crkl* (FIG. 3C) labeling of untreated K562 cancer cells and K562 cells following treatment with dasatinib, in accordance with various embodiments.

This example describes the visualization of activated TK proteins ERK*, STAT3*, STAT5*, ABL*, AKT*, and CRKL* in whole cells from cancer cell lines, and demonstrates that a QD probe assay, properly optimized, may be used to detect elevated levels of specific phosphoproteins that are suppressed by the Gleevec analog, dasatinib. In various embodiments, specific QD probes were developed and optimized for detecting and quantifying several protein kinases. Cancer cells from cell lines and patient white blood cells were screened with a panel of protein-QD probes before and after treatment with the cancer drug dasatinib. Relative amounts of bound QD probes in each condition were estimated using the algorithms described above. FIGS. 3A-3C illustrate digital images of QD-Erk* (FIG. 3A), QD-STAT5* (FIG. 3B), and QD-Crkl* (FIG. 3C) labeling of untreated K562 cancer cells and K562 cells following treatment with dasatinib, in accordance with various embodiments. As predicted, K562 cells treated with dasatinib showed greatly reduced levels of QD-Erk* (FIG. 3A), QD-STAT5* (FIG. 3B), and QD-Crkl* (FIG. 3C) when compared to untreated cells.

Example 5

Quantification of STAT5* Levels in Single Cells as a Marker of the Effectiveness of Dasatanib in Cancer Cell Lines This example describes the visualization of activated TK protein STAT5* in whole cells from cancer cell lines, and demonstrates that a QD probe assay, properly optimized, may be used to detect elevated levels of a specific phosphoprotein that is suppressed by the Gleevec drug analog, dasatinib. FIGS. 4A-4D illustrate a graph showing the number of QD particles per cell in dasatinib-treated and untreated K562 cancer cells (FIG. 4A), a digital image of QD-STAT5* labeling in dasatinib-treated and untreated K562 cancer cells (FIG. 4B), histograms showing the number of QD particles per cell in untreated (FIG. 4C), and dasatinib-treated (FIG. 4D) K562 cancer cells, in accordance with various embodiments. The histograms shown in FIGS. 4C and 4D illustrate that the level of STAT5* may be quantified for populations of single cells. The capability of measuring single cell heterogeneity may be useful for staging cancer in various embodiments.

Example 6

Figure 5A:
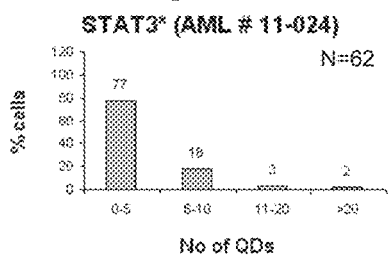
FIGS. 5A-5D illustrate a pair of graphs showing the distribution of QD-STAT3* particles per cell in cells from AML patients (FIG. 5A) and healthy controls (FIG. 5B), and digital images of QD-STAT3* fluorescence in cells from AML patients (FIG. 5C) and healthy controls (FIG. 5D); in accordance with various embodiments.
Figure 5B:
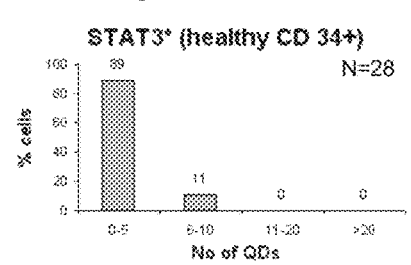
Figure 5C:
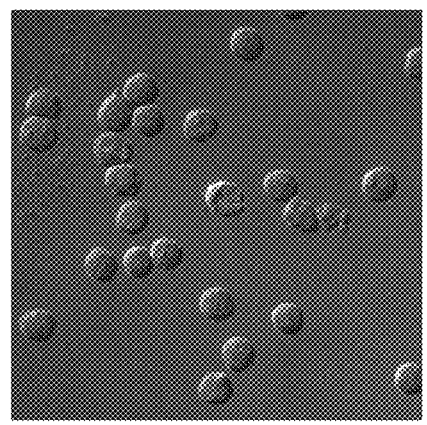
Figure 5D:
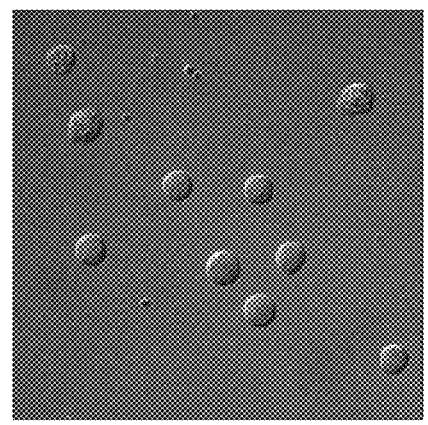

Identification of Elevated Protein Biomarkers in Acute Myeloid Leukemia (AML) Patients This example illustrates the identification of elevated phosphoprotein biomarkers in samples from patients with AML. Mononuclear leukocytes (white blood cells) from healthy individuals (CD34+ MNC) and patients with AML MNC were assayed with QD probes specific for the phosphorylated forms of Abl*, Akt*, Crkl*, ERK*, STAT3*, and STAT5*. FIGS. 5A-5D illustrate a pair of graphs showing the distribution of QD-STAT3* particles per cell in cells from AML patients (FIG. 5A) and healthy controls (FIG. 5B). The number of QDs per cell was much higher in mononuclear lymphocytes from patients with AML as compared to health controls. Similarly, digital images of QD-STAT3* fluorescence in cells from AML patients (FIG. 5C) showed a dramatic increase in QD-STAT3* fluorescence when compared to healthy controls and healthy controls (FIG. 5D).

Figure 6A:
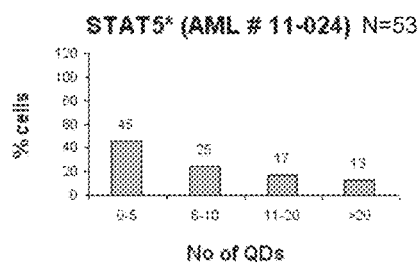
FIGS. 6A-6D illustrate a pair of graphs showing the distribution of QD-STAT5* particles per cell in cells from AML patients (FIG. 6A) and healthy controls (FIG. 6B), and digital images of QD-STAT5* fluorescence in cells from AML patients (FIG. 6C) and healthy controls (FIG. 6D), in accordance with various embodiments.
Figure 6B:
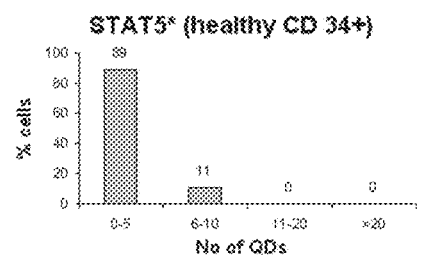
Figure 6C:
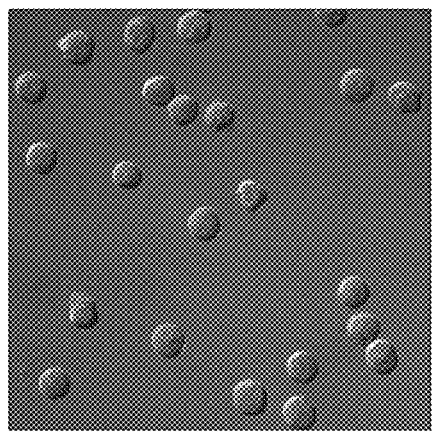
Figure 6D:
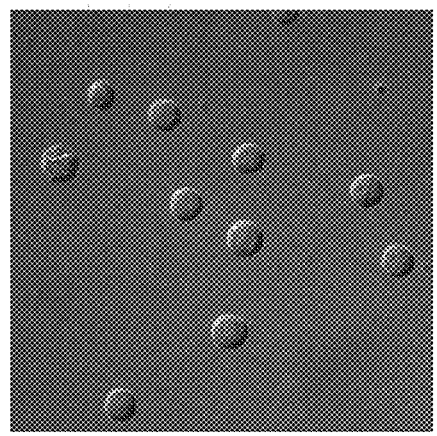

Similar changes were seen with STAT5* labeling in mononuclear leukocytes from AML patients. FIGS. 6A-6D illustrate a pair of graphs showing the distribution of QD-STAT5* particles per cell in cells from AML patients (FIG. 6A) and healthy controls (FIG. 6B), and digital images of QD-STAT5* fluorescence in cells from AML patients (FIG. 6C) and healthy controls (FIG. 6D). Thus, the assays and systems disclosed herein may be used for the accurate and sensitive personalized detection of high levels of STAT5* in an AML patient or individual suspected of having cancer. In some embodiments, STAT5* values from an individual patient may be compared with a reference population or other reference standard.

Example 7

Single QD Probes Quantify Single Cell PP Activity

Figures 10A, 10B, 10C:
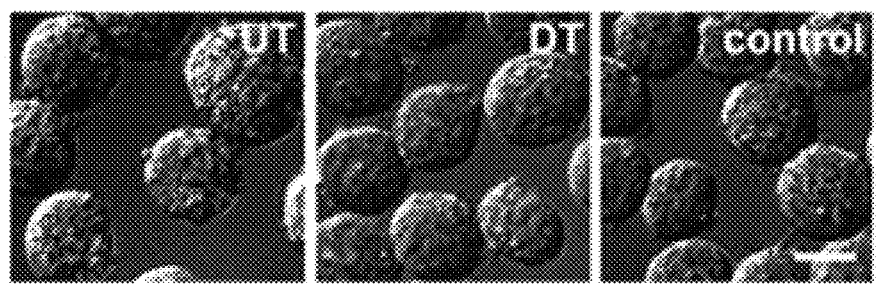
FIGS. 10A-10E include several panels illustrating phosphoprotein activity and spatial compartmentalization in single cells, including a collapsed projection of K562 CML cell lines labeled with QD-pCrkl probes, including are digital images of tumor cells (FIG. 10A), tumor cells treated with dasatinib (FIG. 10B), and control cells with antibody omitted (FIG. 10C), pCrkl and pSTAT5 expression in drug-treated K562 CML cells using Western blot (FIG. 10B) and FACS (FIG. 10C), single cells showing dye-stained plasma membrane and QD-serotonin receptor probes, where algorithms detected plasma membrane and QDs (FIG. 10D), and a histogram showing heterogeneous distribution of single QD-serotonin receptors with predominant plasma-membrane surface expression (FIG. 10E), in accordance with various embodiments.
Figure 10D:
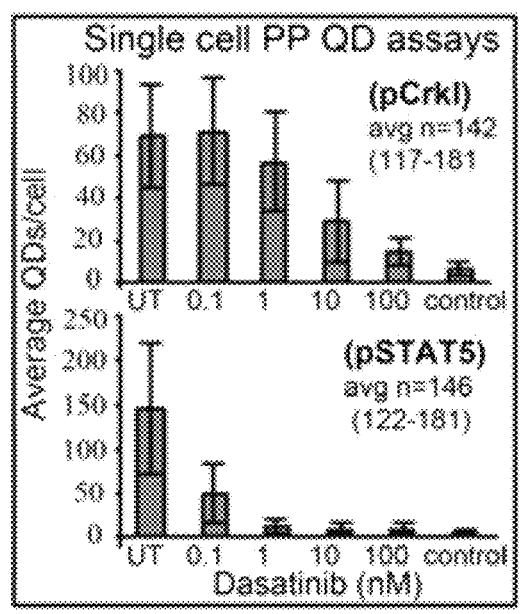
Figure 10E:
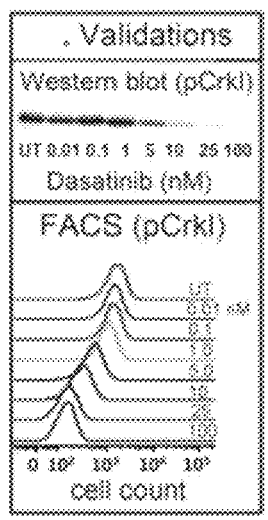

This example illustrates the use of single QD probes that bind to downstream phosphoproteins in CML cell lines that bear the overactive BCR-ABL phospoprotein. An epifluorescent microscope was used to acquire images of cells labeled with QD-pCRKL and QD-pSTAT5 probes, including are digital images of tumor cells (FIG. 10A), tumor cells treated with dasatinib (FIG. 10B), and control cells with antibody omitted (FIG. 10C), Average phosphoprotein levels were computed as the average number of QD probes/cell. These levels decreased with a concomitant increase in dasatinib treatment (a BCR-ABL protein kinase inhibitor), which corresponded to results from Western and FACS assays (FIGS. 10D and 10E). Controls using a non-specific QD-anti-IgG probe indicated that an extremely low level of background binding was achieved (<7 QDs/cell).

Example 8

Algorithms for Locating QD-Tagged Proteins

Figure 10F:
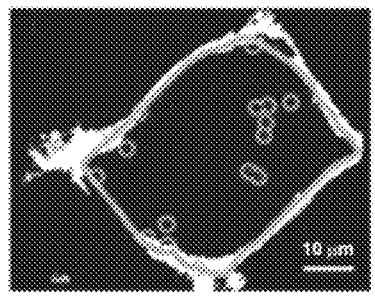
FIGS. 10F and 10G illustrate other algorithms which may be used to identify single cells, to demarcate dye-stained cellular compartments, and to compute the distance between each QD probe and the nearest compartment in accordance with various embodiments.
Figure 10G:
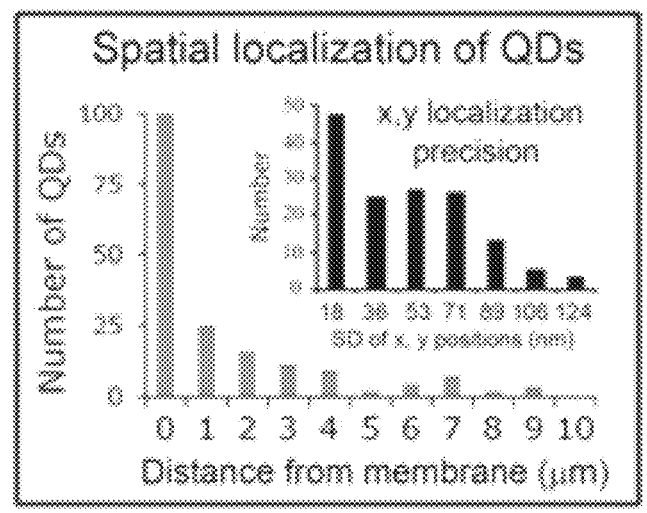

This example illustrates that algorithms may be used for locating QD-tagged proteins with nanometer resolution, and can distinguish between cytosolic and membrane localization. Automated algorithms (e.g., those described above, as well as the exemplary algorithm described in detail in Example 10, below) were used to locate QD-tagged proteins with a spatial resolution of <50 nm (FIG. 10G). Other algorithms may be used to identify single cells, to demarcate dye-stained cellular compartments, and to compute the distance between each QD probe and the nearest compartment (FIGS. 10F and 10G).

Example 9

Use of Single Phosphoprotein-QDs

Figure 11A:
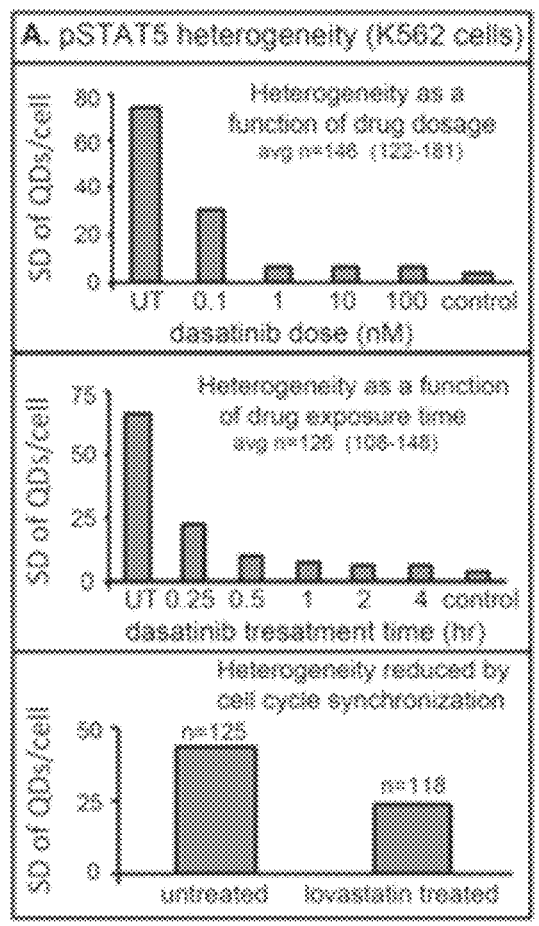
FIGS. 11A-11C illustrate that QD-phosphoprotein probe assays measure phophoprotein response heterogeneity, including that heterogeneity in pSTAT5 activity among clonal K562 CML cells (SD of QDs/cell) was reduced by increasing PKI drug dose and exposure time, as well as lovastatin-induced cell cycle synchronization (FIG. 11A), that multiplexed QD assays detect CD34+ stem cells and pSTAT5 expression in CML blood (FIG. 11B), and that a percentage histogram shows heterogeneity in inhibition of pSTAT5 and pCrkl in CML CD34+ stem cells (FIG. 11C); in accordance with various embodiments.
Figure 11B:
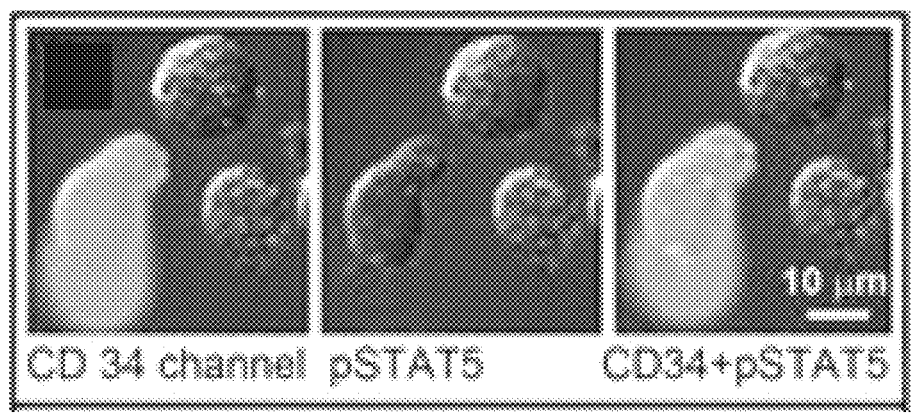
Figure 11C:
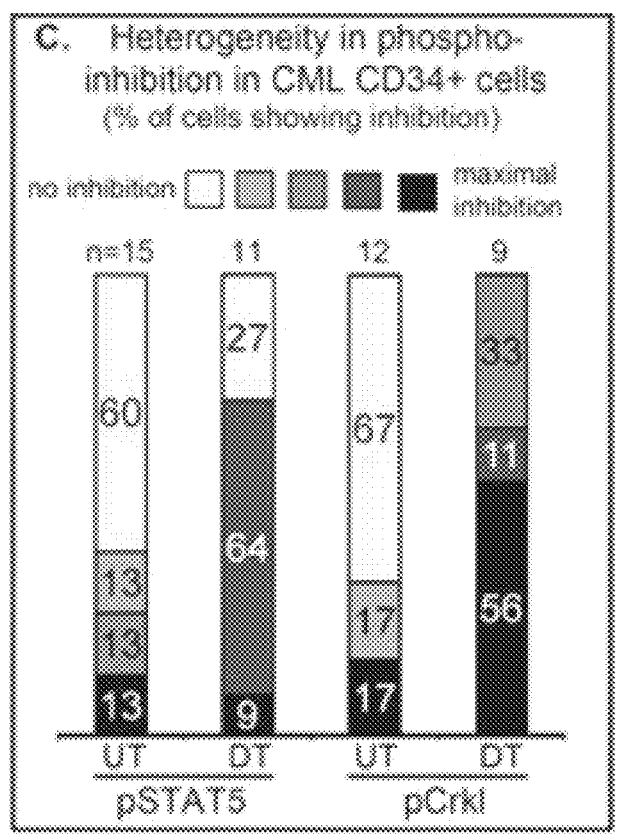

This Example illustrates that single phosphoprotein-QDs can detect differences in phosphoprotein levels, in clonal cell lines and the potential existence of PKI-resistant stem cells in CML patients. As illustrated in the foregoing examples, the phosphoprotein-QD platform can detect subtle differences in pSTAT5 activity in clonal CML cell lines. This heterogeneity was decreased by dasatinib at a controlled duration of exposure. Without being bound by theory, this heterogeneity may be attributed to asynchronous states of cell division among CML clonal cells (FIG. 11A). Phosphoprotein-QD probes also were applied to stem cells from CML patients. Using dual-color QD probes we, rare CD34+ stem cells (~<1% of all hematopoetic cells) were identified, and levels of activated pSTAT5 and pCRKL were identified in these single cells (FIG. 11B). Evidence of heterogeneity in baseline phosphoprotein levels in CD34+ stem cells was found (bars labeled 'DT'; FIG. 11C), and evidence was found for the existence of stem cells with pSTAT5 resistance to dasatinib—a resistance that may differ from the more homogenous cellular protein kinase inhibitor inhibition of pCRKL (bars labeled 'DT'. FIG. 11C).

Example 10

QD Localization

Figure 12:
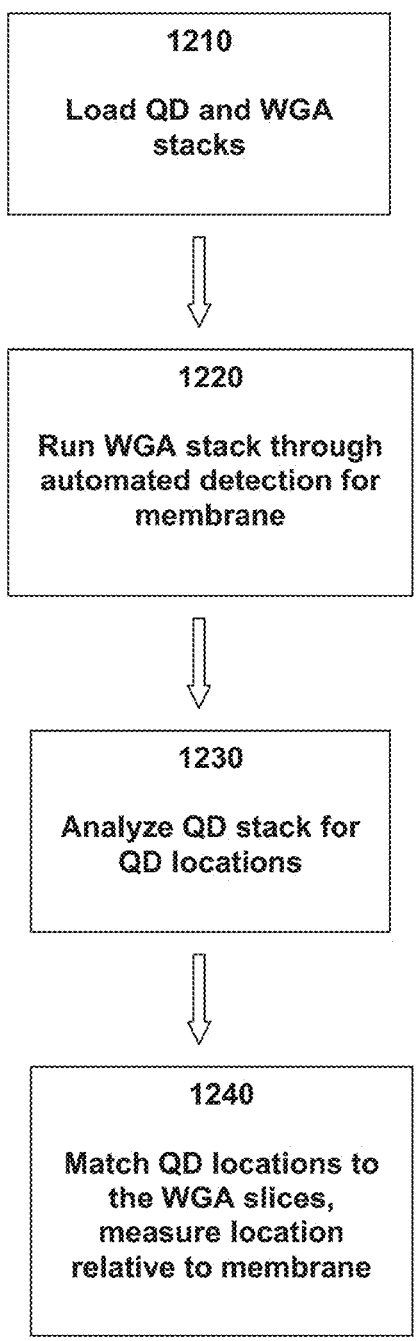
FIG. 12 is a flow chart illustrating a specific, non-limiting example of a method that may be used for locating QDs in a sample, in accordance with various embodiments.
Figure 13:
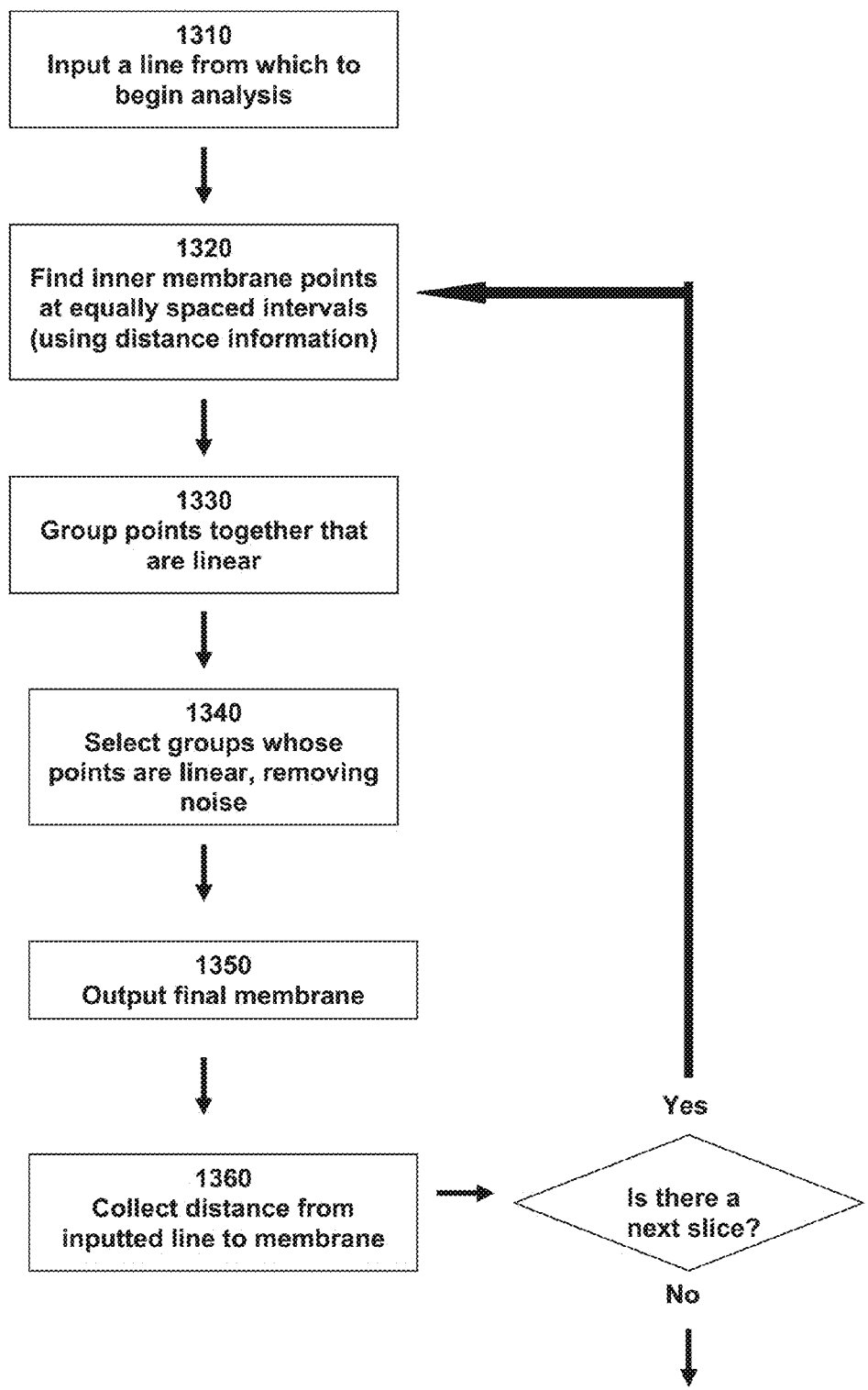
FIG. 13 is a flow chart illustrating a specific, non-limiting example of a method that may be used for automated detection of the membrane (e.g., box 1220 of FIG. 12), in accordance with various embodiments.
Figure 14:
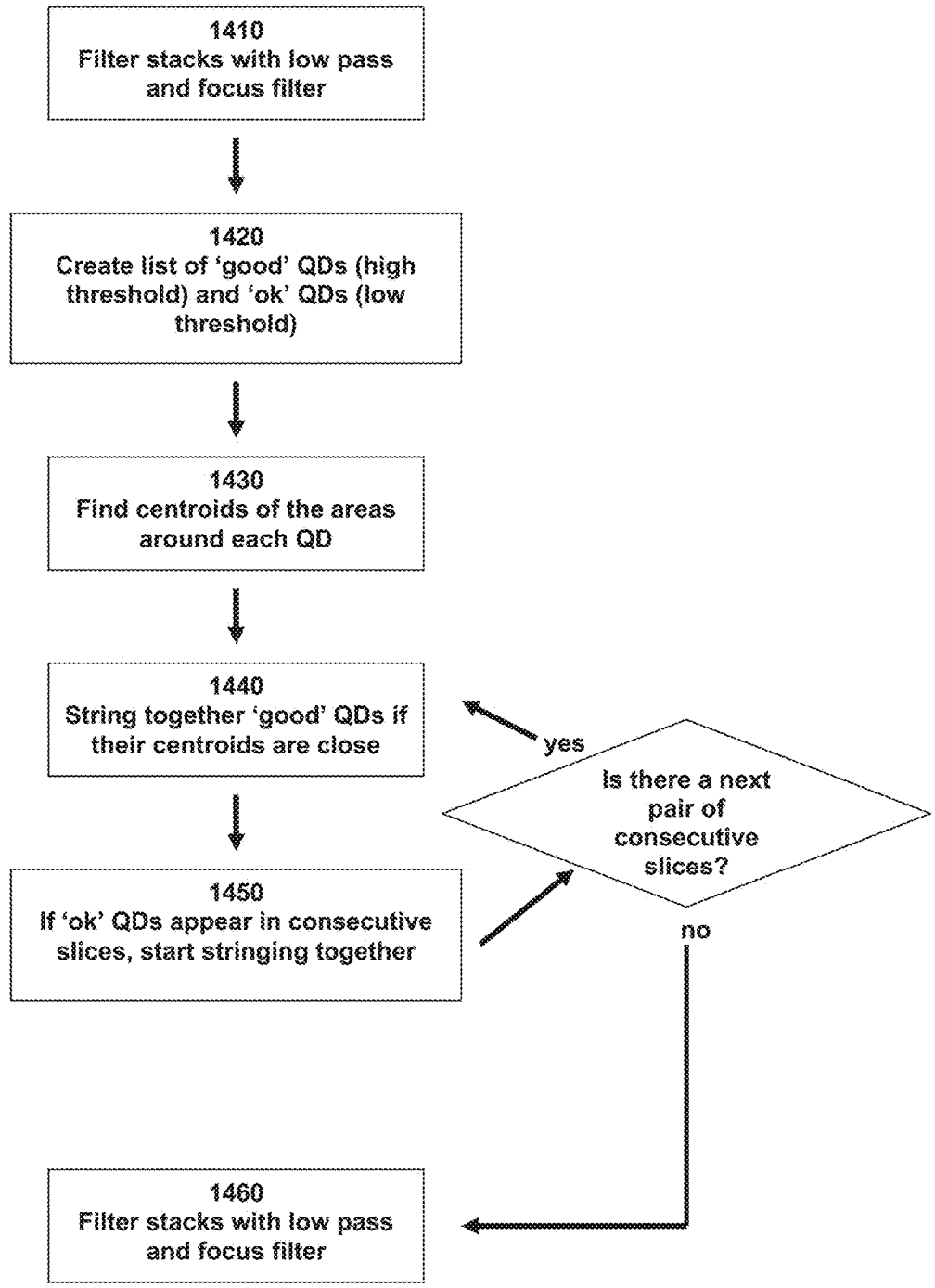
FIG. 14 is a flow chart illustrating a specific, non-limiting example of a method that may be used for analyzing QD stacks of QD locations (e.g., box 1230 of FIG. 12), in accordance with various embodiments.

This example illustrates one specific, non-limiting method for localizing QDs in a sample, which method is illustrated in the flow charts shown in FIGS. 12-14. FIG. 12 is a flow chart illustrating a specific, non-limiting example of a method that may be used for locating QDs in a sample. FIG. 13 is a flow chart illustrating a specific, non-limiting example of a method that may be used for automated detection of the membrane (e.g., box 1220 of FIG. 12), and FIG. 14 is a flow chart illustrating a specific, non-limiting example of a method that may be used for analyzing QD stacks of QD locations (e.g., box 1230 of FIG. 12), all in accordance with various embodiments.

In this example, once a QD stack has been generated, for example using one of the methods described above, a low threshold and an upper threshold are calculated for QD identification in the following steps. Briefly, the mean is defined as the mean of all pixel intensities in 3D stack; the standard deviation is defined as the standard deviation of all pixels with intensity>0 (in some examples, the large number of black pixels throws off the measurement, so they are excluded); the maximum intensity is defined as the maximum pixel intensity in the 3D stack; and the histogram is defined as the cumulative histogram of all pixel intensities greater than 0, with bins with a width of 50 pixels, spanning from 1 to $(2^{16}-1)$. The thresholds are then calculated as follows:

Low threshold=95th percentile on the histogram+2*std

High threshold=(Low threshold+Max)/2

The histogram is then binned with a width of 50 pixels in order to make the process faster (using a value close to 1 would be essentially the same as sorting a list of $\sim 10^6$ values). Because of this, small changes in the percentile used may not change the thresholds at all in some examples. The low threshold may have two standard deviations added to prevent excess noise from being counted as a QD. The 95th percentile value provides a good measure of when the histogram 'tapers off,' so adding two standard deviations ensures that the threshold is not 'too close' to the histogram.

Using the two thresholds, locations for the QDs are then found for each slice of the QD stack. QDs whose intensities are greater than the upper threshold are considered 'good' QDs, while those greater than the lower threshold are considered 'ok' QDs. 'Ok' QDs may represent QDs with just weak intensities, or the locations may just be noise. The 'good' QDs are assumed to be actual QDs.

Next, the locations of potential 'good' QDs are found using the high threshold. In this example, to be a candidate, a pixel must have an intensity greater than the high threshold, and must represent a local maximum, when compared to its locally neighboring pixels in its slice. The candidates for 'good' QDs are then 'cleaned-up,' so that no two maxima are closer than 2*(radius of QD). The centers of these candidates are calculated using the centroid for the area one radius around the pixel, giving sub-pixel localization.

The areas one radius around the 'good' QDs are set to zero, and then these steps are repeated, this time using the low threshold to find the 'ok' QD candidates. A local average (an area one radius around the pixel) and a global average (an area two radii around the pixel, with the area used in the local average set to the image mean) are taken around each of the 'ok' candidates. In some examples, if the local average is greater than 2* global average, the 'ok' candidate may be promoted to a 'good' QD. Conversely, if the local average is less than the global average, then the 'ok' candidate may be removed.

The centers of the 'good' QDs are then re-calculated, now with the added QDs from the 'ok' list. The centers of the 'ok' QDs are calculated in the area 3 radii away from the pixel, and once the center is calculated, if the new center is more than one pixel away from the original pixel, the center is recalculated. This process is continued until the center remains stable. In some examples, two 'look-up' tables may be created for the 'ok' QDs, and for the 'good' QDs, which may improve efficiency when the QD locations are paired in the previous step.

This process may be used to compensate for QDs that are not bright but are well localized, noise in the image that is not well localized, QDs that are near the edge of the image, QDs that are close to other QDs, which could influence the calculation of their centers, and QDs that contain rings around them, where the original position may be on the ring itself.

Once the QD positions have been located as described above, the locations are then paired from slice to slice to create 'strings' of QDs. It may be assumed that the QDs appear in approximately the same location from one slice to the next, which is a good assumption when blinking is taken into account. The result of this process is a set of lists of QD locations, each list corresponding to one QD. This process is iterative, between each pair of consecutive slices, beginning with the top slice. In some examples, an ongoing list of QDs that are being tracked may be maintained, and new QDs may be added for tracking, or a QD location may be added to a QD that is already being tracked. Each 'QD' represents an array of locations, so new locations may be added to a single QD, or a new array altogether may be added. Even if a 'good' QD is not paired, it may be added to the tracking list. An 'ok' QD may only be added to the list once it has been paired with another QD. The QDs in the tracking list are compared with the 'good' QDs in the next slice, and the QDs on the list that are not paired are compared to the 'ok' QDs in the next slice.

If a QD on the list is not paired after the steps outlined above, its 'blink-count' may be incremented, permitting tracking of how long it has been since the QD was last seen. For example, if the 'blink-count' exceeds a predetermined number (for example 2, indicating that it may disappear for up to two slices), then the QD is removed from the tracking list and added to the final QD list (as long as the list itself is long enough). The 'ok' QDs in the current slice are then compared to the 'good' QDs in the next slice. If a pair is found, the two locations are added to the tracking list, and this QD is tracked. The 'ok' QDs not paired in the steps outlined above are then compared to the 'ok' QDs in the next slice. Again, if a pair is found, the two locations are added to the tracking list, and this QD will be tracked. If a good QD in the next slice has not been added yet (possibly because this is the top of a new QD), this QD is added to the tracking list. This process continues for each slice.

Pairing occurs as follows: two QD locations are considered 'close' if a box with a width of the radius of a QD, centered on one of the QDs, overlaps with the other QD. For example, if the radius is set to 3, the two QD locations essentially need to be less than one pixel apart. Throughout the tracking process, the positions of the QDs may be maintained, as well as the beginning and ending slice numbers. This information may prove helpful in debugging, since it allows the coder to see where the program locates the QDs once the program has been run. This is implemented by including a breakpoint after final QD is counted. The final QDs are reset for each ROI. After the QDs have been strung together, a QD must appear in at least 3 slices before it is counted. This ensures that random noise that appears in a few consecutive slices will not be counted as a QD. Because of the minimum number of slices requirement, it is possible that a QD near the top of the stack or near the bottom of the stack will not be counted, since only the 'tail-end' or the beginning of the QD are visible. The result of the process outlined above in a list of QDs, each of which contains its set of (x,y,slice #) coordinates.

In some embodiments, automated membrane detection may be used. This program may be written so that the slices are analyzed layer-by-layer, although information is passed from one layer to the next after it has been completed. The program works by running a loop over another file that analyzes each slice individually. Below is a description of how this code works, and the following section describes how the information is passed from one layer to the next.

Total_trace1.m (essentially line by line)

To begin the program, the user inputs a line onto a chosen slice of the WGA-stained stack of images. From this line, the orientation and length/width are recorded. Next, the image is slightly contrast-enhanced by subtracting the mean value of the image, with the negative values set to zero, ensuring that the areas that are mostly black are set to completely black and making the following operations less noisy.

In the Point Gathering Phase, rays are then drawn out from the inputted line. In one specific, non-limiting example, 300 rays may be drawn. Each ray is associated with an angle, with the angles evenly distributed between 0 and 2S. The originating point for the line moves up and down the inputted line. In one specific, non-limiting example, the $i^{th}$ ray is associated with angle $T_I$, the initial angle of the line is D, the left point of the line is $(x_1,y_1)$, and the right point of the line is $(x_2,y_2)$. Then the x-coordinate of the starting point of the line is set as:

$$x_{start} \frac{x_1 + x_2}{2} + |(x_2\ x_1)|\ \sin(D + T_i)$$

(with the y-coordinate similarly defined.)

The x-coordinate of the ending point of the line is at:

$$x_{end}\ x_{start} + \frac{\max(\text{image\_height, image\_width})}{2} - \cos(D + T_i)$$

(with the y-component similarly defined). Without being bound by theory, the purpose of using the image height/width to define the length of the ray is to put an upper bound on it.

The pixels on the lines are then calculated. Along each line, a profile intensity plot is taken. The first, largest peak, after noise is removed, is assumed to be the membrane, and the left-most edge of the peak is taken as the inside of the membrane. In some examples, the points on this line may be found using a Bresenham-style line algorithm, and the points outside of the image may be removed. In some examples, in order to prevent discrete sampling bias, two more lines may be drawn with small changes to:

$$T_i \left( \text{by a value of } \frac{2S}{2 * \text{num\_points}} \right).$$

The corresponding pixel values are then summed together to create a 1D vector of pixel values along the line.

This vector is passed into get_peak_info to extract the top three peaks. According to the function:

Function—get_peak_info—Arguments: image_data, Returns: Top 3 peaks first, the local maxima are identified. If the peak has a plateau, usually caused by the image being fully saturated, then the leftmost value is used. Next, the minima to the left and right of each maximum are identified. If the minimum is over 90% of the peak value, then the area is smoothed in order to further remove any aliasing effects.

After the smoothing, the local maxima are recounted, and the pixel value for the highest peak is recorded as $I_{max}$. For each peak, the minima to the left and to the right of the maximum are identified. The left value (which is just the index of the point on the line) is $x_{left}$ and the right value is $x_{right}$. If the peak maximum is below a threshold (set earlier), is less than $$\frac{I_{max}}{2},$$

or $|x_{right} \, x_{left}|<6$, then the peak is removed.

A modified version of the data is created consisting only of data between $x_{left}$ and $x_{right}$. The leftmost value in this data above the threshold is set as $p_{final\_left}$ and the rightmost is set as $p_{final\_right}$. These are the values that designate the left and right side of the membrane. In order to get the middle of the membrane, a weighted sum is calculated as $p_{final\_middle}$ $$\frac{\sum x_i I_i}{\sum I_i},$$

where $x_i$ and $I_i$ are the index and intensity of the ith pixel on the modified graph. The different peaks are then sorted by the total pixel sum $\sum I_i$, and the top three peaks are returned, now sorted by increasing $p_{final\_left}$.

The point to use is selected using two matrices, prev_list, which stores the distances from the previous slice from the line to the plasma membrane, and avoid_list, which stores the distances from the previous slice from the line to the nuclear membrane (see find_membrane1.m for details). The point that is chosen from the output of get_peak_info must be within a minimum distance from prev_list (set to 10 now), and further than the same distance from avoid_list, roughly. There are some nuances to this. First, if this is the first slice analyzed, there is no prev_list, so the first point returned by get_peak_info is used instead. If there are no points found close to prev_list and far from avoid_list, then it is assumed that the nuclear membrane is touching the plasma membrane, and the middle value for the peak close to the plasma membrane is used. If there are no points found that meet the criteria, the point is removed.

In the 'Stringing' Phase, the points that are locally linear are grouped together. This is the first phase in removing outliers. The result is a list of strings of points, some of which may still be outliers. To start, the distances between the points and the center of the line are calculated and the first five points are loaded into matrix, which we will call the potential string. The linearity of the potential string is then determined using the function corrCoeff Function—corr_coeff—Arguments: point_list, Returns: True/False if linear If the list of points is too short (fewer than three points), then the line is deemed non-linear. The distances between the (up to) last five points and the center are calculated. The distances are then fit with a line, and the sum of the squares are of the residuals is calculated. If this sum is less than a threshold, currently set to two, then the points are linear, else they are non-linear.

This phase works mostly within a loop over all of the edge points. During each cycle of the loop, the following occurs. If the potential string is non-linear, then points from the end are removed until either the string becomes linear or the string is smaller than two points. If the string is linear, move to the next stage. If the string only has two points, save the two points separately as strings. If the potential string is linear, keep adding points until the string becomes non-linear. Then the potential string is saved and a new string is created.

In the Final Phase, the strings are selected that are linear with respect to each other. The result is the final membrane. First, the longest string is selected. The last 15 points of the string are selected and a linear function is fit to the distances of these points to the center. Next, the points within the next 30 degrees are collected. The first point that has a smaller than 4 pixel distance between it and the regression line is identified. The string that this point is in is added to the final membrane. If there are no points that satisfy the criteria, then the next string of length longer than 3 is found which is then added to the final membrane. After a string is added, a new set of the last 15 points is collected, and the process repeats until the entire membrane is found. Now, a mask can be created of the points. An array of the distances between the center and the edge of the mask is recorded, which is smoothed with a Gaussian filter (size of 5×5, $V^2$ 5) and returned after the completion of total_trace1.m. This array is used in 4 c).

In find_membrane1.m, total_trace1.m takes in an image and a user-drawn line, and then produces a mask of the membrane, and an array of the distances for the image. The function loops over each slice in the stack, calls total_trace1.m, and then moves to the next slice. First, the user inputs a line on a selected slice, from which a mask is drawn and a distance profile is obtained. (Assume for now that the nucleus is not stained.) Then the centroid location $(c_x, c_y)$ and the aspect ratio of the membrane are found. The next slice above is run using Total_trace1.m with the distance profile and the original line, returning a new distance profile and mask.

The line is shifted by the difference in the centroids of the two masks ($*^* c_x$, $*^* c_y$) and stretched by the new aspect ratio. This new line and the distance profile from the last slice are used to produce the next slice's mask. This process continues until it reaches the top of the stack, then it stacks back at the user-inputted slice and works its way downward, until the entire membrane has been found.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein, Therefore, it is manifestly intended that embodiments be limited only by the claims and the equivalents thereof.

What is claimed is:

1. A method of screening a drug for effectiveness in treating leukemia, the method comprising:
   a) contacting a leukemia cell with the drug;
   b) contacting the leukemia cell with a quantum dot labeled antibody specific for phosphorylated Abl, Akt, Crkl, ERK, STAT3, or STAT5;
   c) localizing a set of quantum dots in a 3-dimensional quantum dot image stack of a sample using a computing device by the steps of:
      i) receiving the 3-dimensional quantum dot image stack of the sample, wherein the sample includes a cell and the stack comprises a plurality of slices;
      ii) generating a cumulative histogram of all pixel intensities greater than zero in the quantum dot image stack of the sample;
      iii) calculating a low threshold and a high threshold based on the cumulative histogram;
      iv) identifying a first pixel location of a candidate quantum dot in a first slice of the quantum dot image stack of the sample based on the low threshold and the high threshold;
      v) pairing the first pixel location of the candidate quantum dot with a second pixel location of the candidate quantum dot in a second slice of the quantum dot image stack of the sample, wherein the second slice is adjacent to the first slice and pairing the first or second pixel location of the first candidate quantum dot with a third pixel location of the candidate quantum dot in a third slice of the quantum dot image stack of the sample wherein the third slice is adjacent to either the first slice or the second slice, thereby creating a quantum dot string for the candidate quantum dot;
      vi) detecting a location, in the quantum dot image stack of the sample, of a membrane of the cell using a membrane staining image stack;
      vii) determining the positions of the first and second quantum dots relative to the location of the membrane; and
      viii) outputting a pixel location of the candidate quantum dot and a position of the candidate quantum dot relative to the membrane;
   d) counting the number of quantum dots per cell in a set of the cells using fluorescence microscopy;
   e) wherein a result showing that the average cell has less than 10 quantum dots per cell indicates that the drug is effective in treating leukemia.

2. The method of claim 1 wherein the leukemia cell is derived from a leukemia cell line.

3. The method of claim 2 wherein the cell line is the K562 cell line.

4. The method of claim 1 wherein the leukemia cell is derived from a sample from a subject.

5. The method of claim 1 wherein the drug is a known or putative tyrosine kinase inhibitor.

6. The method of claim 5 wherein the drug is dasatinib or a dasatinib homolog.

7. The method of claim 1, wherein the membrane staining image stack is derived from a membrane-labeled cell.

8. The method of claim 7 wherein the membrane is labeled with wheat germ agglutinin.

9. The method of claim 1 wherein the low threshold is the intensity of the 95th percentile of the distribution of pixel intensity on the histogram +2(standard deviation of the distribution of pixel intensity) and the high threshold=the low threshold+the maximum pixel intensity/2.

10. The method of claim 9 wherein identifying the first pixel location of the candidate quantum dot comprises locating a first pixel that represents both a local maximum of intensity and that exceeds the high threshold.

11. The method of claim 10 further comprising identifying the first pixel location of the candidate quantum dot comprises locating a second pixel that exceeds the low threshold of intensity, exceeds the global intensity average, and is less than the high threshold of intensity.

* * * * *